United States Patent
Polo et al.

(10) Patent No.: US 6,329,201 B1
(45) Date of Patent: *Dec. 11, 2001

(54) COMPOSITIONS AND METHODS FOR PACKAGING OF ALPHAVIRUS VECTORS

(75) Inventors: John M. Polo, Hayward; Thomas W. Dubensky, Jr., Piedmont; Stephen F. Hardy, San Francisco; Silvia Perri, Castro Valley, all of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/609,154

(22) Filed: Jun. 30, 2000

Related U.S. Application Data

(63) Continuation-in-part of application No. 09/476,299, filed on Dec. 30, 1999, now Pat. No. 6,242,259.
(60) Provisional application No. 60/114,732, filed on Dec. 31, 1998.

(51) Int. Cl.[7] ............................. C12N 15/86; C12N 5/10
(52) U.S. Cl. ..................... 435/320.1; 435/325; 435/352
(58) Field of Search ................................ 435/320.1, 325, 435/455, 456, 457, 352; 536/23.1, 23.72; 11/11

(56) References Cited

U.S. PATENT DOCUMENTS 6,242,259 * 6/2001 Polo et al. ............................ 435/456

FOREIGN PATENT DOCUMENTS

| WO 96/37616 | 11/1996 | (WO) . |
| WO 97/38087 | 10/1997 | (WO) . |

OTHER PUBLICATIONS

Dubensky et al., "Sindbis Virus DNA–Based Expression Vectors: Utility for in Vitro and in Vivo Gene Transfer" *J. Virology* 70(1):508–519, Jan., 1996.
Pushko et al., "Replicon–Helper Systems from Attenuated Venezuelan Equine Encephalitis Virus: Expression of Heterologous Genes in Vitro and Immunization Against Heterologous Pathogens in Vivo" *Virology* 239: 389–401, 1997.
Frolov et al., "Sindbis Virus Replicons and Sindbis Virus: Assembly of Chimeras and of Particles Deficient in Virus RNA" *J. Virology* 71 (4): 2819–2829, Apr., 1997.
Frolov et al., "Alphavirus–Based Expression Vectors: Strategies and Applications" *Proc. Natl. Acad. Sci. USA* 93:11371–11377, Oct., 1996.
Polo et al., "Stable Alphavirus Packaging Cell Lines for Sinbid Virus–and Semiliki Forest Virus–Derived Vectors" *Proc. Natl. Acad. Sci. USA* 96:4598–4603, Apr., 1999.
Semerdou and Liljestrom, "Two–Helper RNA System for Production for Recombinant Semliki Forest Virus Particles" *J. Virology* 73(2):1092–1098, Feb., 1999.
Bredenbeek et al., "Sindbis Virus Expression Vectors: Packaging of RNA Replicons by Using Defective Helper RNAs" *J. Virology* 67(11):6439–6446, Nov., 1993.
Berglund et al., "Alphaviruses as Vectors for Gene Delivery" *TIBTECH* 14:130–134, Apr., 1996.
Krug et al., "Enzymatic Synthesis of a 21–Nucleotide Coat Protein Binding Fragment of R17 Ribonucleic Acid" *Biochemistry* 21:4713–4720, 1982.
Schneider et al., "Selection of High Affinity RNA Ligands to the Bacteriophage R17 Coat Protein" *J. Mol. Biol.* 228:862–869, 1992.
Stripecke et al., "Proteins Binding to 5' Untranslated Region Sites: a General Mechanism for Translational Regulation of mRNAs in Human and Yeast Cells" *Mol. Cell. Biol.* 14(9):5898–5909, 1994.
Stripecke and Hentze, "Bacteriophage and Spliceosomal Proteins Function as Position–Dependent Cis/Trans Repressors of mRNA Translation in vitro" *Nucleic Acids Res.* 20(21):5555–5564, 1992.
Werstuck and Green, "Controlling Gene Expression in Living Cells Through Small Molecule–RNA Interactions" *Science* 282:296–298, 1998.

* cited by examiner

*Primary Examiner*—Robert A. Schwartzman
*Assistant Examiner*—Katharine F. Davis
(74) *Attorney, Agent, or Firm*—Louis C. Cullman; Anne S. Dollard; Robert P. Blackburn

(57) ABSTRACT

Nucleic acid molecule are provided comprising a nucleic acid sequence which encodes, in order, an alphavirus capsid, a signal peptide, and an alphavirus E1 or E2 glycoprotein. Also provided are vectors encoding such nucleic acid molecules, and use of such vectors or expression cassettes to generate recombinant alphavirus particles and alphavirus packaging cell lines. In addition, modified alphavirus vector constructs are provided that permit reduced transgene expression during vector packaging, as well as methods of using such vector constructs for the production of alphavirus vector particles.

10 Claims, 10 Drawing Sheets

Sequences for Binding of R17 Ligand

```
                              U  C              U  C    A
                           A        A        A        A
       U₁₂ U₁₃             C - G             C - G
  A₁₁       A₁₄            C - G             C - G
    G₁₀- C₁₅            A  C - G          A  C - G
    G₉ - C₁₆                G - C             U - A
  A₈            
    G₇ - C₁₇               A - U             G - C
    U₆ - A₁₈               C - G             A - U
    A₅ - U₁₉               C - G             U - A
    C₄ - G₂₀             AUAGU              A
    A₃ - U₂₁
  A₁ A₂
```

MS2 operator      5TOP      TOP

FIG. 7

Reduced transgene expression in an alphavirus packaging cell line expressing the R17 coat protein
CPPCL 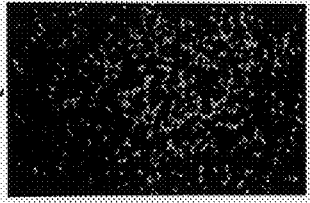 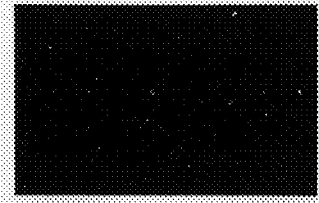 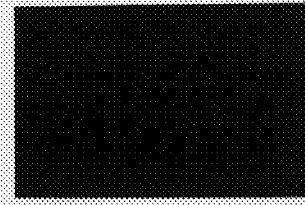
PCL 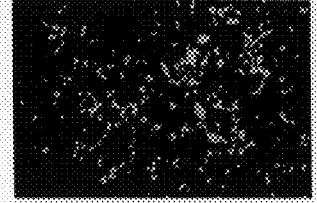 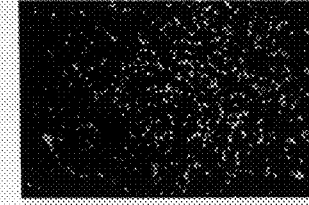 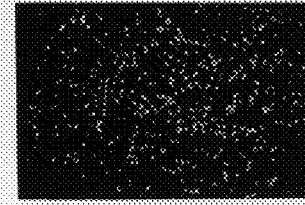
SINCR     TOP     5TOP
FIG. 9

Reduced transgene expression in an alphavirus packaging cell line expressing the R17 coat protein

FIG. 10

COMPOSITIONS AND METHODS FOR PACKAGING OF ALPHAVIRUS VECTORS

CROSS-REFERENCE TO RELATED APPLICATION

This application is a continuation-in-part of U.S. patent application Ser. No. 09/476,299, filed Dec. 30, 1999, now U.S. Pat. No. 6,242,259 which application claims priority to U.S. Provisional Patent Application No. 60/114,732 filed Dec. 31, 1998 which application is incorporated by reference in its entirety.

TECHNICAL FIELD

The present invention relates generally to recombinant DNA technology; and more specifically, to the development of packaging systems for the high level production of recombinant alphavirus vector particles useful for directing expression of one or more heterologous gene products.

BACKGROUND OF THE INVENTION

Alphaviruses comprise a group of genetically, structurally, and serologically related arthropod-borne viruses of the Togaviridae family. These viruses are distributed worldwide, and persist in nature through a mosquito to vertebrate cycle. Birds, rodents, horses, primates, and humans are among the defined alphavirus vertebrate reservoir/hosts.

Twenty-six known viruses and virus subtypes have been classified within the alphavirus genus utilizing the hemagglutination inhibition (HI) assay. This assay segregates the 26 alphaviruses into three major complexes: the Venezuelan equine encephalitis (VEE) complex, the Semliki Forest (SF) complex, and the western equine encephalitis (WEE) complex. In addition, four other viruses, eastern equine encephalitis (EEE), Barmah Forest, Middelburg, and Ndumu, receive individual classification based on the HI serological assay.

Members of the alphavirus genus also are classified based on their relative clinical features in humans: alphaviruses associated primarily with encephalitis, and alphaviruses associated primarily with fever, rash, and polyarthritis. Included in the former group are the VEE and WEE complexes, and EEE. In general, infection with this group can result in permanent sequelae, including death. In the latter group is the SF complex, comprised of the individual alphaviruses Semliki Forest, Sindbis, Ross River, Chikungunya, O'nyong-nyong, and Mayaro. Although serious epidemics have been reported, infection by viruses of this group is generally self-limiting, without permanent sequelae.

Sindbis virus is the prototype member of the Alphavirus genus of the Togaviridae family. Its replication strategy is well characterized and serves as a model for other alphaviruses (Strauss and Strauss, 1994, *Microbio. Rev.*, 58:491–562). The genome of Sindbis virus (like other alphaviruses) is an approximately 12 kb single-stranded, positive-sense RNA molecule that is capped and polyadenylated. Genome RNA is contained within a virus-encoded capsid protein shell which is, in turn, surrounded by a host-derived lipid envelope from which two viral-specific glycoproteins, E1 and E2, protrude as spikes from the virion surface. Certain alphaviruses (e.g., SF) also maintain an additional protein, E3, which is a cleavage product from the E2 precursor protein, PE2.

After virus particle absorption to target cells, penetration, and uncoating of the nucleocapsid to release viral genomic RNA into the cytoplasm, the replication process is initiated by translation of four nonstructural replicase proteins (nsP1–nsP4) from the 5' two-thirds of the viral genome. The four nsPs are translated as one of two polyproteins (nsP123 or nsP1234), and processed post-translationally into mature monomeric proteins by an active protease in the C-terminal domain of nsP2. Both of the nonstructural polyproteins and their derived monomeric units may participate in the RNA replication process, which involves nsP binding to the conserved nucleotide sequence elements (CSEs) present at the 5' and 3' ends, and an internal subgenomic junction region promoter.

The positive strand genome RNA serves as template for the nsP-catalyzed synthesis of a full-length complementary negative strand RNA. Synthesis of the negative strand RNA is catalyzed by binding of an nsP complex to the 3' terminal CSE of the positive strand genome RNA. The negative strand, in turn, serves as template for the synthesis of additional positive strand genome RNA, as well as an abundant subgenomic RNA, initiated internally at the junction region promoter. Synthesis of additional positive strand genome RNA occurs after binding of an nsP complex to the 3' terminal CSE of the complementary negative strand genome-length RNA template. Synthesis of the subgenomic mRNA from the negative strand RNA template is initiated from the junction region promoter. Thus, the 5' end and junction region CSEs of the positive strand genome RNA are functional only after being transcribed into the negative strand RNA complement (i.e., the 5' end CSE is functional when it is the 3' end of the genomic negative stranded complement).

Alphavirus structural proteins (sPs) are translated from the subgenomic RNA, which represents the 3' one-third of the genome, and like the nsPs, are processed post-translationally into the individual proteins (FIG. 1). Translation of this subgenomic mRNA produces a single polyprotein consisting of the structural proteins capsid (C) glycoprotein E2 and glycoprotein E1, plus the corresponding leader/signal sequences (E3, 6k) for glycoprotein insertion into the endoplasmic reticulum. The structural gene polyprotein is processed into the mature protein species by a combination of viral (capsid autoprotease) and cellular proteases (e.g., signal peptidase). Alphavirus structural proteins are produced at very high levels due to the abundance of subgenomic mRNA transcribed, as well as the presence of a translational enhancer element (Frolov and Schlesinger, 1994, *J. Virol.* 68:8111–8117; Sjoberg et al., 1994, *Bio/Technol.* 12:1127–1131) within the mRNA, located in the capsid gene coding sequence. Because all structural proteins are synthesized at equimolar ratios, as part of the polyprotein, the translation enhancer element exerts its effect equally on each of the genes.

The general strategy for construction of alphavirus-based expression vectors has been to substitute the viral structural protein genes with a heterologous gene, maintaining transcriptional control via the highly active subgenomic RNA promoter. Vectors of this configuration are termed RNA "replicons" and may be transcribed in vitro from cDNA using a bacteriophage promoter, or, generated in vivo directly from DNA when linked to a eukaryotic promoter. Currently, alphavirus replicon RNA is packaged into recombinant vector particles by transient co-transfection with in vitro transcribed defective helper RNA, or, using stable packaging cell lines having structural protein expression cassettes. The structural protein expression cassette(s) used for vector packaging encode either the intact "native" alphavirus structural polyprotein that is post-translationally processed into mature C, E2, and E1; or, alphavirus structural proteins that have been split into separate cassettes encoding either C or E2/E1.

As described in the detailed description and examples below, the present invention provides new compositions and methods for packaging of alphavirus particles, including novel alphavirus structural polyprotein genes, expression cassettes containing the genes, polypeptides expressed from the cassettes, and methods of using the genes, cassettes, and polypeptides for the high level packaging of alphavirus vector RNA into recombinant alphavirus vector particles in the absence of contaminating replication-competent virus. The invention also provides modifications to alphavirus vector systems wherein expression of the heterologous transgene from an alphavirus vector replicon may be reduced (suppressed) in desired cells, including during the vector packaging process. This specific reduction in transgene expression can provide a mechanism to increase the level of recombinant alphavirus vector particles produced in those instances where the transgene has a negative effect on replicon particle titer.

SUMMARY OF THE INVENTION

Briefly stated, the present invention provides methods for generating high titer recombinant alphavirus particle preparations in the absence of contaminating replication-competent virus, as well as the generation of stable alphavirus packaging cells. Within one aspect of the invention nucleic acid molecules are provided wherein the molecule encodes an alphavirus envelope glycoprotein E2 or E1 independent of the other glycoprotein, and as an in-frame fusion with a leader/signal peptide sequence of alphavirus (e.g., E3, 6K) or non-alphavirus (e.g., TPA) origin.

In another aspect of the invention nucleic acid molecules are provided wherein the molecule encodes in a single open-reading frame (ORF), a polypeptide that is a polyprotein comprising in order, an alphavirus capsid protein, a leader/signal peptide, and an alphavirus glycoprotein E2, with the proviso that the molecule does not encode an alphavirus glycoprotein E1. In one embodiment, the leader/signal sequence is an alphavirus E3 peptide. In another embodiment, the leader/signal sequence is of non-alphavirus origin.

In another aspect of the invention nucleic acid molecules are provided wherein the molecule encodes in a single open-reading frame (ORF), a polypeptide that is a polyprotein comprising in order, an alphavirus capsid protein, a leader/signal peptide, and an alphavirus glycoprotein E1, with the proviso that the molecule does not encode an alphavirus glycoprotein E2. In one embodiment, the encoded leader/signal peptide is an alphavirus E3 peptide. In another embodiment, the encoded leader/signal peptide is an alphavirus 6K peptide. In yet another embodiment, the encoded leader/signal peptide is of non-alphavirus origin.

In another aspect of the invention nucleic acid molecules are provided wherein the molecule encodes a single open-reading frame (ORF), a polypeptide that is a polyprotein comprising in order, an alphavirus capsid protein, a first leader/signal peptide, a second leader/signal peptide, and an alphavirus glycoprotein E1. In a preferred embodiment, the first encoded leader/signal peptide is an alphavirus E3 peptide and the second encoded leader/signal peptide is an alphavirus 6K peptide. Within this aspect it is preferred that the nucleic acid molecule not encode an alphavirus E2 protein.

Within any of the above-noted aspects, the nucleic acid molecules provided herein may be 'isolated' (i.e., not integrated into the genomic DNA of an organism, or, in the case of a virus, is separated from the complete virus genome). Within preferred embodiments, the nucleic acid molecules provided herein do not contain all elements of the wild-type structural polyprotein gene (i.e., C, E3, E2, 6k and E1) in order.

In other aspects of the invention expression cassettes are provided wherein the cassette directs the expression of an alphavirus structural polypeptide of the present invention. In preferred embodiments, the cassette directs the expression of a polypeptide that is a polyprotein selected from the group consisting of 1) an alphavirus capsid protein, a leader/signal peptide, and an alphavirus glycoprotein E2; 2) an alphavirus capsid protein, a leader/signal peptide, and an alphavirus glycoprotein E1; 3) an alphavirus capsid protein, a first leader/signal peptide, a second leader/signal peptide, and an alphavirus glycoprotein E1; and 4) an alphavirus capsid protein, a first leader/signal peptide, a second leader/signal peptide, and an alphavirus glycoprotein E2. In particularly preferred embodiments, the cassette directs the expression of a polypeptide that is a polyprotein selected from the group consisting of 1) an alphavirus capsid protein, an alphavirus E3 peptide, and an alphavirus glycoprotein E2; 2) an alphavirus capsid protein, a leader/signal peptide of non-alphavirus origin, and an alphavirus glycoprotein E1; 3) an alphavirus capsid protein, an alphavirus E3 peptide, and an alphavirus glycoprotein E1; 4) an alphavirus capsid protein, an alphavirus 6K peptide, and an alphavirus glycoprotein E1; and 5) an alphavirus capsid protein, an alphavirus E3 peptide, an alphavirus 6K peptide, and an alphavirus glycoprotein E1.

In one embodiment, alphavirus structural protein expression cassettes of the present invention are provided wherein the cassette comprises a DNA promoter of RNA transcription (e.g., RNA polymerase II promoter) operably linked to a structural protein open reading frame (ORF), and a transcription termination/polyadenylation sequence.

In another embodiment, the alphavirus structural protein expression cassette is an alphavirus defective helper RNA transcribed in vitro or in vivo, comprising the ordered elements: 5' viral or defective-interfering RNA sequence required in cis for alphaviral replication (also referred to as 5' CSE, or, the "5' sequence which initiates transcription of alphavirus RNA", in the background), viral subgenomic junction region promoter, alphavirus structural protein gene sequence of the present invention, 3' alphaviral sequence required in cis for replication (also referred to as 3' CSE or the "3' alphavirus RNA polymerase recognition sequence", in the background), and, optionally, a polyadenylate tract. Preferably, such expression cassettes do not encode all functional non-structural proteins. Within further embodiments, the expression cassette is a cDNA further comprising a 5' promoter upstream of the expression cassette which can provide transcription of the expression cassette (e.g., in vitro, or alternatively, in a eukaryotic cell) and optionally a transcription termination site downstream of the cassette.

In yet another embodiment, the alphavirus structural protein expression cassette is a DNA cassette comprising the ordered elements: DNA promoter of RNA transcription that functions within a eukaryotic cell (e.g., RNA polymerase II promoter), 5' viral or defective-interfering RNA sequence required in cis for alphaviral replication, viral subgenomic junction region promoter, alphavirus structural protein sequence of the present invention, 3' alphaviral sequence required in cis for replication, polyadenylate tract, and transcription termination/polyadenylation sequence.

In another aspect of the invention, alphavirus structural polypeptides are provided wherein the polypeptides are polyproteins selected from the group consisting of: 1) an alphavirus capsid protein, an alphavirus E3 peptide, and an alphavirus glycoprotein E2; 2) an alphavirus capsid protein, a leader/signal peptide of non-alphavirus origin, and an alphavirus glycoprotein E1; 3) an alphavirus capsid protein, an alphavirus E3 peptide, and an alphavirus glycoprotein E1; 4) an alphavirus capsid protein, an alphavirus 6K peptide, and an alphavirus glycoprotein E1; and 5) an alphavirus capsid protein, an alphavirus E3 peptide, an alphavirus 6K peptide, and an alphavirus glycoprotein E1.

In another aspect, expression cassettes are provided comprising a promoter which is operably linked to a nucleic acid molecule, which when transcribed produces an RNA sequence complementary ("antisense") to an alphavirus junction region promoter, or, alphavirus subgenomic mRNA, wherein said nucleic acid molecule is less than 500, 250, 100, or 50 nucleotides in length. Preferably the RNA sequence complementary to an alphavirus subgenomic RNA is complementary to at least a portion of the 5' end non-translated region and translation initiation codon of the subgenomic RNA. Also provided in other aspects are host cells which contain such expression cassettes, and alphavirus packaging cell lines which contain such expression cassettes.

In another aspect of the invention, host cells are provided which contain the alphavirus expression cassettes described herein. In preferred embodiments, the cells are stably transformed with the structural protein expression cassettes or cassettes that transcribe complementary ("antisense") RNA. In particularly preferred embodiments, the cells are of mammalian origin and are alphavirus packaging cells.

Within certain embodiments of the invention, the elements of the alphavirus expression cassettes may be selected from different alphaviruses (e.g., a packaging cell may be comprised of a first alphavirus expression cassette: C, E3, E2 and a second alphavirus expression cassette: C, 6k, E1, wherein E3 and 6k are from different alphaviruses). Within certain embodiments the two expression cassettes may be placed onto a single vector (e.g., with opposite and divergent transcriptional orientation).

Within other aspects of the present invention alphavirus packaging cells are provided, comprising (a) a first expression cassette which directs the expression of a first nucleic acid molecule, comprising a nucleic acid sequence which encodes, in order, an alphavirus capsid, a signal peptide, and an alphavirus E1 glycoprotein, with the proviso that the first nucleic acid molecule does not encode an alphavirus E2 glycoprotein; and (b) a second expression cassette which directs the expression of a second nucleic acid molecule, comprising a nucleic acid sequence which encodes, in order, an alphavirus capsid, a signal peptide, and an alphavirus E2 glycoprotein, with the proviso that the second nucleic acid molecule does not encode an alphavirus E1 glycoprotein. Within various embodiments the signal peptide may be an alphavirus signal peptide (e.g. an alphavirus E3 peptide or an alphavirus 6k peptide), or, a non-alphavirus signal peptide (e.g., a tissue plasminogen activator, TPA, signal peptide). Within further embodiments, the signal peptide of the first or second expression cassette is a first signal peptide, and that cassette further comprises an additional, second signal peptide (which may be of alphavirus or non-alphavirus origin, as discussed above).

Within related aspects alphavirus packaging cell lines are provided comprising one or more alphavirus structural protein expression cassettes and an expression cassette comprising a promoter that is operably linked to a nucleic acid molecule, which when transcribed produces an RNA sequence complementary to an alphavirus junction region promoter, or, alphavirus subgenomic RNA, wherein said nucleic acid molecule is less than 500 nucleotides in length. Within related aspects, alphavirus packaging cell lines are also provided comprising one or more alphavirus structural protein expression cassettes and an expression cassette comprising a promoter that is operably linked to a nucleic acid molecule which encodes R17 coat protein.

Within further aspects of the invention, methods of producing alphavirus particles are provided herein, comprising the step of introducing into a packaging cell line as described herein a vector selected from the group consisting of alphavirus vector constructs, RNA vector replicons, eukaryotic layered vector initiation systems (e.g., U.S. Pat. No. 5,814,482), and alphavirus vector particles, such that recombinant alphavirus vector particles are produced.

Within another aspect of the invention methods of producing alphavirus vector particles are provided, comprising introducing into a host cell (a) a first expression cassette which directs the expression of a first nucleic acid molecule, comprising a nucleic acid sequence which encodes, in order, an alphavirus capsid, a signal peptide, and an alphavirus E1 glycoprotein, with the proviso that the first nucleic acid molecule does not encode an alphavirus E2 glycoprotein; and (b) a second expression cassette which directs the expression of a second nucleic acid molecule, comprising a nucleic acid sequence which encodes, in order, an alphavirus capsid, a signal peptide, and an alphavirus E2 glycoprotein, with the proviso that the second nucleic acid molecule does not encode an alphavirus E1 glycoprotein; and (c) a vector selected from the group consisting of alphavirus vector constructs, RNA vector replicons, eukaryotic layered vector initiation systems, and alphavirus vector particles; such that alphavirus vector particles are produced. In one embodiment, the expression cassettes (a) and/or (b) are introduced into a host cell as DNA molecules. In another embodiment, the expression cassettes (a) and/or (b) are introduced into a host cell as in vitro transcribed RNA.

Within various embodiments, methods of producing recombinant alphavirus particles are provided comprising introducing into a population of cells (a) an alphavirus vector construct, RNA vector replicon, eukaryotic layered vector initiation system, or, recombinant alphavirus particle, (b) one or more alphavirus structural protein expression cassettes, and (c) an RNA sequence complementary ("antisense") to an alphavirus junction region promoter, or alphavirus subgenomic RNA. In preferred embodiments, the complementary RNA sequence is introduced as an expression cassette that transcribes within the population of cells the complementary RNA sequence.

In another aspect of the invention, methods of packaging recombinant alphavirus vector particles are provided, comprising introducing into a population of cells (a) an alphavirus vector construct or vector RNA replicon, (b) an alphavirus structural protein expression cassette described herein encoding capsid and glycoprotein E2, and (c) an alphavirus structural protein expression cassette described herein encoding capsid and glycoprotein E1, such that recombinant alphavirus particles are produced. In preferred embodiments, the alphavirus structural protein expression cassettes encoding capsid and glycoprotein E2 or E1 are defective helper RNA transcribed in vitro or in vivo. In particularly preferred embodiments, the cells are alphavirus packaging cells.

In yet another aspect of the invention, preparations of alphavirus vector particles free from contaminating replication-competent virus are provided, wherein the vector particles are obtained by the method comprising introducing into a population of cells (a) an alphavirus vector construct or vector RNA replicon, (b) an alphavirus structural protein expression cassette described herein encoding capsid and glycoprotein E2, and (c) an alphavirus structural protein expression cassette described herein encoding capsid and glycoprotein E1, such that recombinant alphavirus particles are produced. In preferred embodiments, the alphavirus vector particle preparations are obtained by said method wherein the alphavirus structural protein expression cassettes encoding capsid and glycoprotein E2 and E1 are defective helper RNA transcribed in vitro or in vivo. In particularly preferred embodiments, the alphavirus vector particle preparations are obtained by said method wherein the cells are alphavirus packaging cells.

Within other aspects of the invention RNA vector replicons are provided, comprising: a 5' sequence which initiates transcription of alphavirus RNA; a nucleic acid sequence that codes for biologically active alphavirus nonstructural proteins; an alphavirus subgenomic junction region promoter; a non-alphavirus nucleotide sequence which, when bound by a ligand reduces transcription of subgenomic RNA or translation of a heterologous gene of interest (i.e., "transgene") encoded by the subgenomic RNA; a heterologous gene of interest; and a 3' alphavirus RNA polymerase recognition sequence.

Within other aspects, RNA vector replicons are provided comprising a 5' sequence which initiates transcription of alphavirus RNA; a nucleic acid sequence that codes for biologically active alphavirus nonstructural proteins from a first alphavirus; an alphavirus subgenomic junction region promoter; an alphavirus nucleotide sequence which, when bound by a ligand or complementary ("antisense") RNA reduces transcription of subgenomic RNA or translation of a heterologous gene of interest encoded by the subgenomic RNA, wherein said alphavirus nucleotide sequence is from a second alphavirus different from said first alphavirus; a heterologous gene of interest; and a 3' alphavirus RNA polymerase recognition sequence.

Within another aspect of the invention RNA vectors are provided comprising a 5' sequence which initiates transcription of alphavirus RNA; an alphavirus subgenomic junction region promoter, a non-alphavirus nucleotide sequence which, when bound by a ligand reduces transcription of subgenomic RNA or translation of a heterologous gene of interest encoded by the subgenomic RNA, a heterologous gene of interest; and a 3' alphavirus RNA polymerase recognition sequence, wherein said RNA vector does not encode all biologically active alphavirus nonstructural proteins.

Within yet another aspect of the present invention RNA vectors are provided comprising a 5' sequence which initiates transcription of alphavirus RNA; an alphavirus subgenomic junction region promoter, an alphavirus nucleotide sequence which, when bound by a ligand reduces transcription of subgenomic RNA or translation of a heterologous gene of interest encoded by the subgenomic RNA, a heterologous gene of interest and a 3' alphavirus RNA polymerase recognition sequence, wherein said 5' sequence which initiates transcription and said 3' alphavirus RNA polymerase recognition sequence are from a first alphavirus, and the alphavirus nucleotide sequence is from a second alphavirus different from said first alphavirus, and wherein said RNA vector does not encode all biologically active alphavirus nonstructural proteins.

Within preferred embodiments of the invention, the above-noted RNA vector replicons and RNA vectors are comprised of elements that are ordered in the manner set forth above.

A wide variety of non-alphavirus (i.e., not obtained or derived from an alphavirus) nucleotide sequences may be specifically selected and utilized within the context of the present invention. For example, within certain embodiments of the above aspects, the non-alphavirus nucleotide sequence is a binding site for an RNA binding protein, such as, for example an R17 coat binding protein, or comprises a sequence as shown in FIG. 7 (i.e., STOP or TOP). Within other embodiments the non-alphavirus nucleotide sequence is a binding site for an antibiotic (e.g., tobramycin), or a binding site for Hoechst dyes (e.g., H33258 or H33342).

Within further embodiments the alphavirus nucleotide sequence is a sequence from a subgenomic 5' end nontranslated region of VEE.

Within related embodiments of the invention, the ligand may be an RNA binding protein (e.g., RI 7 coat protein), an antisense sequence, a dye (e.g., Hoechst dyes H33258 or H3342) or an antibiotic.

Within yet further embodiments the ligand may be an antisense nucleic acid sequence.

As utilized within the context of the present invention, a reduction of either transcription of subgenomic RNA, or, a reduction of translation of a heterologous gene of interest (or "transgene") encoded by the subgenomic RNA, should be understood to refer to a statistically significant decrease of either transcription, or, translation respectively, in the presence of the selected ligand. . In particularly preferred embodiments, the level of either transcription of subgenomic RNA, or, level of heterologous transgene expression in cells is reduced at least 25%, 50%, 75%, or 90%, or 3-fold, 5-fold, or 10-fold as compared to the level of expression without the presence of the binding ligand. A wide variety of assays may be utilized to assess a reduced level of transcription or translation, including for example, enzymatic assays of a reporter gene, northern blots, metabolic RNA labeling, as well as the assays provided in Example 8.

Within other embodiments of the invention, the alphavirus nucleotide sequence from the second alphavirus comprises the complement of a sequence from a subgenomic 5' end non-translated region of an alphavirus, and wherein the alphavirus sequence is less than 500, 250, 100, or, 50 nucleotides in length. Within other embodiments, the alphavirus nucleotide sequence comprises a portion of an alphavirus RNA vector replicon subgenomic junction region promoter, and wherein the alphavirus nucleotide sequence is less than 500, 250, 100, or, 50 nucleotides in length. Within various embodiments, the alphavirus nucleotide sequence is positioned downstream from the subgenomic junction region promoter of the RNA vector, or, upstream from the heterologous gene of interest. Within further embodiments, the first alphavirus may be Sindbis virus or Semliki Forest virus, and the second alphavirus can be VEE.

Within further aspects of the invention, RNA vector replicons are provided comprising a 5' sequence which initiates transcription of alphavirus RNA, nucleic acid sequences that code for biologically active alphavirus nonstructural proteins, an alphavirus subgenomic junction region promoter, a sequence from a subgenomic 5' end nontranslated region from VEE, a heterologous gene of interest and a 3' alphavirus RNA polymerase recognition sequence, with the proviso that said nonstructural proteins are not from VEE. In preferred embodiments, the nonstructural proteins are from Sindbis virus or Semliki Forest virus.

Within a related aspect, RNA vectors are provided comprising a 5' sequence which initiates transcription of alphavirus RNA, an alphavirus subgenomic junction region promoter, a sequence from a subgenomic 5' end nontranslated region from VEE, a heterologous gene of interest and a 3' alphavirus RNA polymerase recognition sequence, wherein the vector does not encode all biologically active alphavirus nonstructural proteins, and wherein said 5' sequence which initiates transcription and said 3' alphavirus RNA polymerase recognition sequence are not from VEE.

Within another related aspect, RNA vectors are provided comprising a 5' sequence which initiates transcription of alphavirus RNA, an alphavirus subgenomic junction region promoter, a sequence from a subgenomic 5' end nontranslated region from VEE, one or more alphavirus structural proteins and a 3' alphavirus RNA polymerase recognition sequence, wherein the vector does not encode all biologically active alphavirus nonstructural proteins, and wherein the alphavirus structural protein(s) are not from VEE.

In other aspects, the above RNA vectors comprising a VEE 5' end nontranslated region are transcribed from a DNA molecule in vitro (e.g., from a bacteriophage promoter) or within a eukaryotic cell (e.g., from an RNA polymerase II promoter).

Within various embodiments of the above, the RNA vectors provided herein may further comprise a polyadenylation tract. Within other embodiments of the invention, the non-alphavirus sequence in the RNA vector of RNA vector replicons provided herein are not internal ribosome entry sites "IRES" or ribosomal readthrough sequences).

Within other aspects of the invention, alphavirus vector constructs are provided, comprising a 5' promoter operably linked to a nucleic acid molecule, wherein said nucleic acid molecule is complementary DNA to the RNA vectors described herein. As utilized within this context, it should be understood that an RNA vector refers to an RNA molecule which may be either an RNA vector replicon as described herein, or, an RNA molecule which, unlike the RNA vector replicon lacks all sequences necessary for biologically active alphavirus nonstructural proteins (e.g., is a defective helper construct). Within certain embodiments, the promoter can be a eukaryotic promoter, or, a bacteriophage promoter.

Other aspects of the present invention provide methods of producing packaged alphavirus vector particles wherein the level of expression of a heterologous transgene from an alphavirus vector construct or vector RNA replicon is reduced in cells used for packaging as compared to the level of expression in a target cell. In preferred embodiments, the method of reducing expression of a heterologous transgene from the alphavirus vector is by reducing transcription from the subgenomic junction region promoter or reducing translation from the subgenomic mRNA. In particularly preferred embodiments, the level of heterologous transgene expression in cells used for packaging is reduced at least 25%, 50%, 75%, or 90%, or 3-fold, 5-fold, or 10-fold as compared to the level of expression in a target cell.

In one embodiment, a method of producing alphavirus vector particles is provided, comprising introducing into a population of cells (a) an alphavirus vector construct, RNA vector replicon, eukaryotic layered vector initiation system, or, recombinant alphavirus particle, (b) an alphavirus structural protein expression cassette described herein encoding capsid and glycoprotein E2, and (c) an alphavirus structural protein expression cassette described herein encoding capsid and glycoprotein E1, such that recombinant alphavirus particles are produced, wherein the cells further contain a complementary RNA sequence (e.g., antisense) of the present invention, the sequence being complementary to the junction region promoter or subgenomic RNA of the alphavirus vector RNA. In preferred embodiments, the complementary or antisense RNA sequence is expressed from a cassette within the cells and the cells are stably transformed with said cassette that expresses an antisense RNA. In another embodiment, cells are provided wherein the cells contain a cassette that expresses an RNA sequence complementary to (e.g., antisense) the junction region promoter or subgenomic RNA of an alphavirus vector, with the proviso that the cells are permissive for alphavirus vector RNA replication.

In another embodiment, a method of producing alphavirus vector particles is provided, comprising introducing into a population of cells (a) an alphavirus vector construct, vector RNA replicon, eukaryotic layered vector initiation system or recombinant alphavirus particle (b) an alphavirus structural protein expression cassette encoding capsid but not glycoproteins E2 or E1, and (c) an alphavirus structural protein expression cassette encoding glycoproteins E2 and E1 but not capsid, such that recombinant alphavirus particles are produced, wherein the cells further contain a complementary RNA sequence (e.g., antisense) of the present invention, said sequence being complementary to the junction region promoter or subgenomic RNA of the alphavirus vector RNA. In preferred embodiments, the complementary or antisense RNA sequence is expressed from a cassette within the cells and the cells are stably transformed with said cassette that expresses an antisense RNA. In another embodiment, cells are provided wherein the cells contain a cassette that expresses an RNA sequence complementary to (e.g., antisense) the junction region promoter or subgenomic RNA of an alphavirus vector, with the proviso that the cells are permissive for alphavirus vector RNA replication.

In a further embodiment, a method of producing alphavirus vector particles is provided, comprising introducing into a population of cells (a) an alphavirus vector construct, RNA vector replicon, eukaryotic layered vector initiation system, or recombinant alphavirus particle, (b) an alphavirus structural protein expression cassette described herein encoding capsid and glycoprotein E2, and (c) an alphavirus structural protein expression cassette described herein encoding capsid and glycoprotein E1, such that recombinant alphavirus particles are produced, wherein the alphavirus vector construct, RNA vector replicon, eukaryotic layered vector initiation system, or alphavirus particle further comprises an RNA aptamer sequence that binds to a ligand provided, therein reducing translation from the subgenomic RNA, said RNA aptamer being inserted within the vector sequence corresponding to said subgenomic RNA. As utilized herein, an RNA aptamer should be understood to refer to a non-alphavirus nucleotide sequence that is one member of a ligand binding pair that reduces or prevents translation of the alphavirus vector subgenomic RNA, as compared to wild-type alphavirus, in the presence of a ligand.

In another embodiment, a method of producing alphavirus vector particles is provided, comprising introducing into a population of cells (a) an alphavirus vector construct, RNA vector replicon, eukaryotic layered vector initiation system, or alphavirus particle, (b) an alphavirus structural protein expression cassette encoding capsid but not glycoproteins E2 and E1, and (c) an alphavirus structural protein expression cassette encoding glycoproteins E2 and E1 but not capsid, such that recombinant alphavirus particles are produced, wherein the alphavirus vector construct, RNA vector replicon, eukaryotic layered vector initiation system, or alphavirus particle further comprises an RNA aptamer sequence that binds to a ligand provided, therein reducing translation from the subgenomic RNA, said RNA aptamer being inserted within the vector sequence corresponding to said subgenomic RNA. As utilized herein, an RNA aptamer should be understood to refer to a non-alphavirus nucleotide sequence that is one member of a ligand binding pair that reduces or prevents translation of the alphavirus vector subgenomic RNA, as compared to wild-type alphavirus, in the presence of a ligand.

In preferred embodiments, the RNA aptamer within the alphavirus vector construct or vector RNA replicon binds to a ligand that is an antibiotic. In particularly preferred embodiments, the RNA aptamer binds to Tobramycin or Kanamycin.

In another preferred embodiment, the RNA aptamer within the alphavirus vector construct or vector RNA replicon binds to Hoechst dyes H33258 or H33342.

Also provided within the present invention are alphavirus vector constructs, RNA vector replicons, eukaryotic layered vector initiation systems, and alphavirus particles which further comprise an RNA aptamer sequence that binds to a ligand, therein reducing translation from the vector subgenomic RNA, said RNA aptamer being inserted within the vector sequence corresponding to said subgenomic RNA. In preferred embodiments the RNA aptamer binds to an antibiotic or Hoechst dyes H33258 or H33342.

Within further embodiments of the invention, methods are provided for suppressing expression of a transgene (or desired heterologous sequence) during the generation of recombinant alphavirus particles from a packaging or producer cell line, by culturing the packaging or producer cell line with the second member of the ligand binding pair (the ligand) which binds the RNA apatamer, thus preventing or reducing expression of the transgene (or desired heterologous sequence). In one embodiment, the ligand may be an antisense RNA molecule.

Within yet other aspects of the invention, methods are provided for reducing transcription of subgenomic RNA or translation of a heterologous gene of interest encoded by subgenomic RNA of an alphavirus RNA vector replicon or alphavirus vector construct, comprising the steps of introducing into a cell (a) an RNA vector or alphavirus vector construct as described herein; and (b) an expression cassette which directs the expression of a ligand that reduces transcription of subgenomic RNA or translation of a heterologous gene of interest encoded by the subgenomic RNA according to the present invention, such that transcription of subgenomic RNA or translation of a heterologous gene of interest encoded by subgenomic RNA is reduced. Within various embodiments, the ligand is an R17 coat protein, or, an antisense sequence. Within other embodiments, the cell is an alphavirus packaging cell.

These and other aspects of the present invention will become evident upon reference to the following detailed description and attached drawings. In addition, various references are identified below which describe in more detail various compositions (e.g., plasmids or cell lines) and methods, and therefore are herein expressly incorporated by reference in their entirety.

BRIEF DESCRIPTION OF THE DRAWINGS

FIG. 7 is an illustration of sequence modifications (SEQ ID NOs: 41, 50 and 51) to an alphavirus vector that allow for binding of a bacteriophage protein.

FIG. 9 is a series of photographs by fluorescence microscopy, which show reduced expression of an alphavirus replicon-encoded heterologous transgene in a packaging cell line that expresses the R17 coat protein.

FIG. 10 is a graph demonstrating reduced expression of an alphavirus replicon-encoded heterologous transgene in a packaging cell line that expresses the R17 coat protein.

DETAILED DESCRIPTION OF THE INVENTION

Definitions

Figure 1:
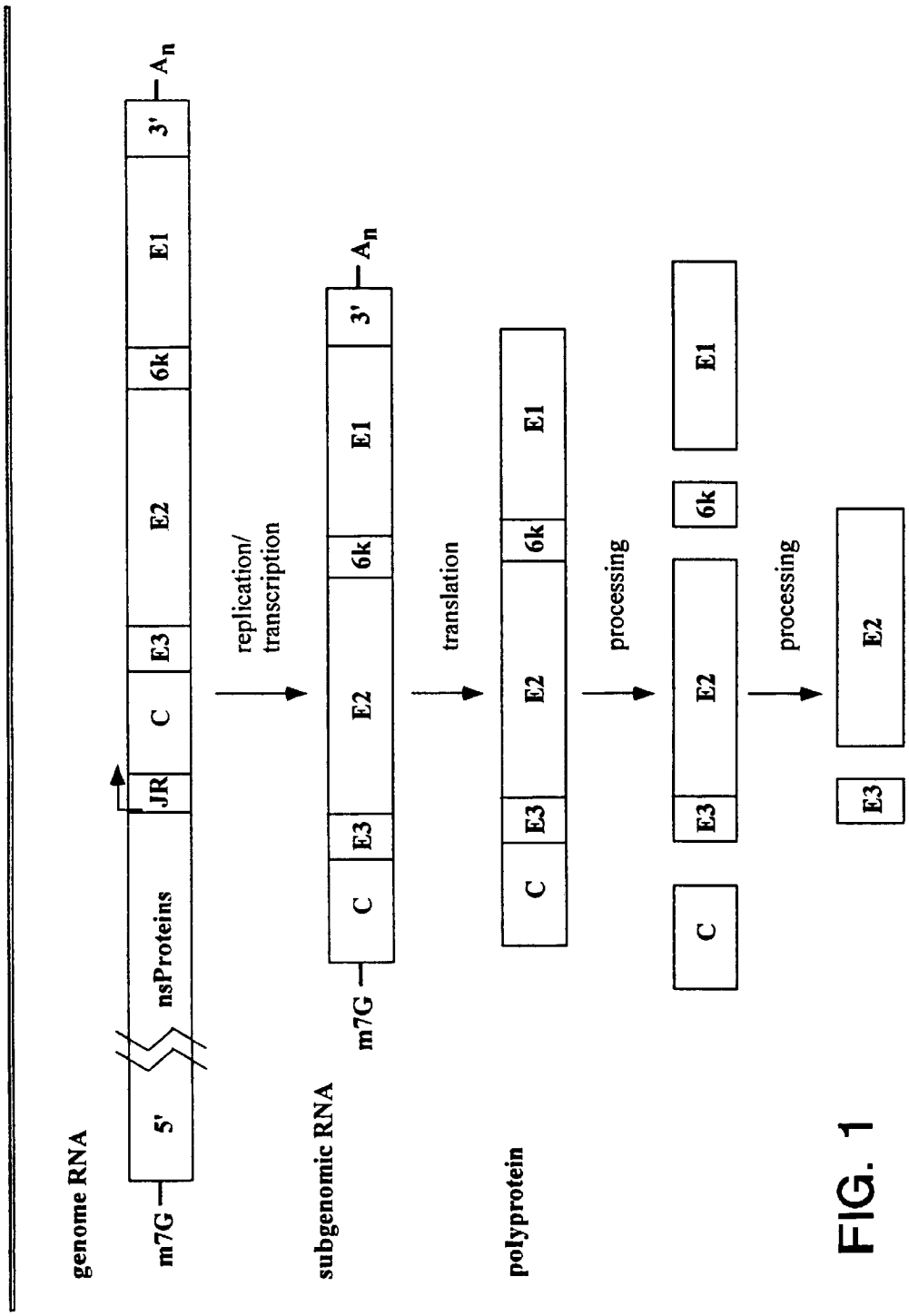
FIG. 1 is a schematic illustration of the expression and processing of a wild-type alphavirus structural polyprotein.

The following terms are used throughout the specification. Unless otherwise indicated, these terms are defined as follows:

An "isolated nucleic acid molecule" is a nucleic acid molecule that is not integrated into the genomic DNA of an organism, or, in the case of a virus, is separated from the complete virus genome. One example of an isolated nucleic acid molecule is a chemically-synthesized nucleic acid molecule, or, a nucleic acid molecule that is produced by recombinant (e.g., PCR) techniques.

"Genomic RNA" refers to an RNA that contains all of the genetic information required to direct its own amplification or self-replication in vivo, within a target cell. An alphavirus-derived genomic RNA molecule should contain the following ordered elements: 5' viral or defective-interfering RNA sequence(s) required in cis for replication, sequences which, when expressed, code for biologically active alphavirus nonstructural proteins (e.g., nsP1, nsP2, nsP3, nsP4), 3' viral sequences required in cis for replication, and a polyadenylate tract. The alphavirus-derived genomic RNA vector replicon may also contain a viral subgenomic "junction region" promoter and sequences which, when expressed, code for biologically active alphavirus structural proteins (e.g., C, E3, E2, 6K, E1). Generally, the term genomic RNA refers to a molecule of positive polarity, or "message" sense, and the genomic RNA may be of length different from that of any known, naturally-occurring alphavirus.

"Subgenomic RNA" refers to an RNA molecule of a length or size which is smaller than the genomic RNA from which it was derived. Subgenomic RNA is transcribed from an internal promoter whose sequences reside within the genomic RNA or its complement. In preferred embodiments, the subgenomic RNA is produced from an alphavirus vector construct, RNA vector replicon, or defective helper construct and encodes one or more alphavirus structural proteins or other heterologous sequences of interest. Generally, the subgenomic RNA resembles a typical mRNA with 5' and 3' end non-translated regions and a protein encoding open reading frame.

"Alphavirus vector construct" refers to an assembly which is capable of directing the expression of a sequence or gene of interest. Such vector constructs are comprised of a 5' sequence which is capable of initiating transcription of an alphavirus RNA (also referred to as 5° CSE, or, 5' sequence which is capable of initiating transcription of an alphavirus RNA, in the background), as well as sequences which, when expressed, code for biologically active alphavirus nonstructural proteins (e.g., nsP1, nsP2, nsP3, nsP4), an alphavirus RNA polymerase recognition sequence (also referred to as 3' CSE, or, alphavirus RNA polymerase recognition sequence, in the background), and, optionally a polyadenylate tract. In addition, the vector construct may include a viral subgenomic "junction region" promoter, sequences from one or more structural protein genes or portions thereof, extraneous nucleic acid molecule(s) which are of a size sufficient to allow production of viable virus, a 5' promoter which is capable of initiating the synthesis of viral RNA from cDNA in vitro or in vivo, a heterologous sequence to be expressed, and one or more restriction sites for insertion of heterologous sequences.

"Alphavirus RNA vector replicon", "RNA vector replicon" and "replicon" refers to an RNA molecule which is capable of directing its own amplification or self-replication in vivo, within a target cell. An alphavirus-derived RNA vector replicon should contain the following ordered elements: 5' viral sequences required in cis for replication (also referred to as 5' CSE, in background), sequences which, when expressed, code for biologically active alphavirus nonstructural proteins (e.g., nsP1, nsP2, nsP3, nsP4), 3' viral sequences required in cis for replication (also referred to as 3' CSE, in background), and a polyadenylate tract. The alphavirus-derived RNA vector replicon may also contain a viral subgenomic "junction region" promoter, sequences from one or more structural protein genes or portions thereof, extraneous nucleic acid molecule(s) which are of a size sufficient to allow production of recombinant alphavirus particles, as well as heterologous sequence(s) to be expressed.

"Recombinant Alphavirus Particle" refers to a virion-like structural unit containing an alphavirus RNA vector replicon. Generally, a recombinant alphavirus particle comprises one or more alphavirus structural proteins, a lipid envelope and an RNA vector replicon. Preferably, the recombinant alphavirus particle contains a nucleocapsid structure that is contained within a host cell-derived lipid bilayer, such as a plasma membrane, in which alphaviral-encoded envelope glycoproteins are embedded. The particle may also contain other components (e.g., targeting elements, other viral structural proteins, or other receptor binding ligands) which direct the tropism of the particle from which the alphavirus was derived.

"Structural protein expression cassette" refers to a nucleic acid molecule that is capable of directing the synthesis of one or more alphavirus structural proteins. The expression cassette should include a 5' promoter which is capable of initiating the synthesis of RNA from cDNA, as well as sequences which, when expressed, code for one or more biologically active alphavirus structural proteins (e.g., C, E3, E2, 6K, E1), and a 3' sequence which controls transcription termination. The expression cassette also may include a 5' sequence which is capable of initiating transcription of an alphavirus RNA (also referred to as 5' CSE, in background), a viral subgenomic "junction region" promoter, an alphavirus RNA polymerase recognition sequence (also referred to as 3' CSE, in background), and a polyadenylate tract. In certain embodiments, the expression cassette also may include splice recognition sequences, a catalytic ribozyme processing sequence, a sequence encoding a selectable marker, or a nuclear export signal. In addition, expression of the alphavirus structural protein(s) may, in certain embodiments, be regulated by the use of an inducible promoter.

"Stable Transformation" refers to the introduction of a nucleic acid molecule into a living cell, and long-term or permanent maintenance of that nucleic acid molecule in progeny cells through successive cycles of cell division. The nucleic acid molecule may be maintained in any cellular compartment, including, but not limited to, the nucleus, mitochondria, or cytoplasm. In preferred embodiments, the nucleic acid molecule is maintained in the nucleus. Maintenance may be intrachromosomal (integrated) or extrachromosomal, as an episomal event.

"Alphavirus packaging cell line" refers to a cell which contains an alphavirus structural protein expression cassette and which produces recombinant alphavirus particles after introduction of an alphavirus vector construct, RNA vector replicon, eukaryotic layered vector initiation system (e.g., U.S. Pat. No. 5,814,482), or recombinant alphavirus particle. The parental cell may be of mammalian or non-mammalian origin. Within preferred embodiments, the packaging cell line is stably transformed with the structural protein expression cassette.

"Defective helper construct" refers to an assembly which is capable of RNA amplification or replication, and expression of one or more alphavirus structural proteins in response to biologically active alphavirus nonstructural proteins supplied in trans. The defective helper construct should contain the following ordered elements: 5' viral or defective-interfering RNA sequences required in cis for replication (also referred to as 5' CSE, in background), a viral subgenomic junction region promoter, sequences which, when expressed, code for one or more biologically active alphavirus structural proteins (e.g., C, E3, E2, 6K, E1), 3' viral sequences required in cis for replication (also referred to as 3' CSE, in background), and a polyadenylate tract. The defective helper construct may also contain a 5' promoter which is capable of initiating the synthesis of viral RNA from cDNA in vitro or in vivo, a 3' sequence which controls transcription termination, splice recognition sequences, a catalytic ribozyme processing sequence, a sequence encoding a selectable marker, and a nuclear export signal. A defective helper construct should not encode all four functional alphavirus nonstructural proteins.

"Eukaryotic Layered Vector Initiation System" refers to an assembly which is capable of directing the expression of a sequence(s) or gene(s) of interest. The eukaryotic layered vector initiation system should contain a 5' promoter which is capable of initiating in vivo (i.e., within a cell) the synthesis of RNA from cDNA, and a viral vector sequence which is capable of directing its own replication in a eukaryotic cell and also expressing a heterologous sequence. In preferred embodiments, the nucleic acid vector sequence is an alphavirus-derived sequence and is comprised of a 5' sequence which is capable of initiating transcription of an alphavirus RNA (also referred to as 5' CSE, in background), as well as sequences which, when expressed, code for biologically active alphavirus nonstructural proteins (e.g., nsP1, nsP2, nsP3, nsP4), and an alphavirus RNA polymerase recognition sequence (also referred to as 3' CSE, in background). In addition, the vector sequence may include a viral subgenomic "junction region" promoter, sequences from one or more structural protein genes or portions thereof, extraneous nucleic acid molecule(s) which are of a size sufficient to allow optimal amplification, a heterologous sequence to be expressed, one or more restriction sites for insertion of heterologous sequences, as well as a polyadenylation sequence. The eukaryotic layered vector initiation system may also contain splice recognition sequences, a catalytic ribozyme processing sequence, a nuclear export signal, and a transcription termination sequence. (See U.S. Pat. No. 5,814,482 or PCT Publication No. WO 97/38087.)

"Polyprotein" refers to a single polypeptide comprising two or more proteins, wherein the polypeptide is processed by proteases into the individual proteins during or after translation of the polypeptide. The polyprotein should be encoded by one open-reading frame (ORF) within an mRNA molecule, and may be naturally occurring or generated using recombinant DNA techniques by combining separate genes (e.g., removing translation initiator or terminator codons as necessary) and inserting appropriate signals for processing of the polyprotein into individual protein species.

"Leader/signal peptide" refers to a peptide sequence contained within a polypeptide, which is necessary for transport of the polypeptide into/across the endoplasmic reticulum (ER) membrane. In preferred embodiments, the leader/signal peptide is located at the amino-terminus of the polypeptide and is cleaved from the remainder of the polypeptide (e.g., by signal peptidase) after its function for ER transport has been performed.

As discussed in more detail below, the present invention provides: (A) sources of wild-type alphaviruses suitable for constructing the nucleic acid sequences, expression cassettes, polypeptides and vectors; (B) alphavirus vector constructs and alphavirus RNA vector replicons; (C) alphavirus structural polyprotein genes; (D) expression cassettes containing alphavirus structural polyprotein genes; (E) alphavirus packaging cell lines; (F) methods of packaging recombinant alphavirus particles; (G) methods of suppressing heterologous gene expression during vector packaging; and (H) heterologous sequences (also referred to as "transgenes") which may be expressed within the context of the present invention.

A. Sources of Alphaviruses

As noted above, the present invention provides a wide variety of alphavirus-derived nucleic acid sequences, expression cassettes, polypeptides, and vectors, as well as methods for utilizing such sequences, cassettes, and polypeptides for high level packaging of the vectors into recombinant alphavirus vector particles in the absence of contaminating replication-competent virus. Briefly, sequences encoding alphaviruses suitable for use in preparing the above-described compositions can be readily obtained given the disclosure provided herein from naturally occurring sources, or from depositories (e.g., the American Type Culture Collection, Rockville, Maryland). Representative examples of suitable alphaviruses are described in more detail in U.S. Pat. No. 5,843,723 and PCT Publication No. WO 97/38087.

B. Alphavirus Vector Constructs and Alphavirus RNA Vector Replicons

As noted above, the present invention provides both DNA and RNA vector constructs which are derived from alphaviruses. Briefly, within one aspect of the present invention alphavirus vector constructs are provided, comprising a 5' promoter which initiates synthesis of viral RNA from cDNA, a 5' sequence which initiates transcription of alphavirus RNA, a nucleic acid sequence encoding all four alphaviral nonstructural proteins, an alphavirus RNA polymerase recognition sequence and a 3' polyadenylate tract. Within other aspects, RNA vector replicons are provided, comprising a 5' sequence which initiates transcription of alphavirus RNA, a nucleic acid sequence which encodes all four alphaviral nonstructural proteins, an alphavirus RNA polymerase recognition sequence and a 3' polyadenylate tract. Within preferred embodiments of the above, the above constructs further comprise a viral junction region. Each of these aspects is discussed in more detail below (see also Strauss and Strauss, *Microbiol. Rev.* 58(3):491–562, 1994).

1. 5' Promoters which initiate synthesis of viral RNA

As noted above, within certain embodiments of the invention, alphavirus vector constructs and defective helper constructs are provided which contain 5' promoters (e.g., DNA dependent RNA polymerase promoters) that initiate synthesis of viral RNA from cDNA by a process of in vitro transcription. Within preferred embodiments such promoters include, for example, the bacteriophage T7, T3, and SP6 RNA polymerase promoters. Similarly, alphavirus vector constructs and defective helper constructs are provided which contain 5' promoters (e.g., DNA dependent RNA polymerase promoters) that initiate synthesis of viral RNA from cDNA in vivo (i.e., within a cell). Within certain embodiments, such RNA polymerase promoters may be derived from both prokaryotic and eukaryotic organisms, and include, for example, the bacterial β-galactosidase and trpE promoters, and the eukaryotic viral simian virus 40 (SV40) (e.g., early or late), cytomegalovirus (CMV) (e.g., immediate early), Moloney murine leukemia virus (MoMLV) or Rous sarcoma virus (RSV) LTR, and herpes simplex virus (HSV) (thymidine kinase) promoters.

2. Sequences Which Initiate Transcription

As noted above, within preferred embodiments, the alphavirus vector constructs, RNA vector replicons and defective helper constructs of the present invention contain a 5' sequence which is capable of initiating transcription of an alphavirus RNA (also referred to as 5'-end CSE, or 5' cis replication sequence). Representative examples of such sequences include nucleotides 1–60, and to a lesser extent nucleotides through bases 150–210, of the Sindbis virus, nucleotides 10–75 for tRNA$^{Asp}$ (aspartic acid, U.S. Pat. No. 5,091,309), and 5' sequences from other alphaviruses which initiate transcription. It is the complement of these sequences, which corresponds to the 3' end of the of the minus-strand genomic copy, which are bound by the alphavirus nonstructural protein "replicase" complex, and possibly additional host cell factors, from which transcription of the positive-strand genomic RNA is initiated.

3. Alphavirus Nonstructural Proteins

The alphavirus vector constructs and RNA vector replicons provided herein also require sequences encoding all four alphaviral nonstructural proteins. Briefly, a wide variety of sequences which encode alphavirus nonstructural proteins, in addition to those explicitly provided herein, may be utilized in the present invention, and are therefore deemed to fall within the scope of the phrase "alphavirus nonstructural proteins." For example, due to the degeneracy of the genetic code, more than one codon may code for a given amino acid. Therefore, a wide variety of nucleic acid sequences which encode alphavirus nonstructural proteins may be generated. Furthermore, amino acid substitutions, additions, or deletions at any of numerous positions may still provide functional or biologically active nonstructural proteins. Within the context of the present invention, alphavirus nonstructural proteins are deemed to be biologically active if they promote self-replication of the vector construct, i.e., replication of viral nucleic acids and not necessarily the production of infectious virus, and may be readily determined by metabolic labeling or RNase protection assays performed over a time course. Methods for making such derivatives are readily accomplished by one of ordinary skill in the art given the disclosure provided herein.

Alphaviruses express four nonstructural proteins, designated nsP1, nsP2, nsP3, and nsP4. Vectors of the present invention derived from alphaviruses should contain sequences encoding the four nonstructural proteins. In wild-type Sindbis virus, nonstructural proteins 1–3 are encoded by nucleotides 60 to 5747, while nsP4 is encoded by nucleotides 5769 to 7598. The nonstructural proteins are translated from the genomic positive strand RNA as one of two large polyproteins, known as P123 or P1234, respectively, depending upon (i) whether there is an opal termination codon between the coding regions of nsP3 and nsP4 and (ii) if there is such an opal codon present, whether there is translation termination of the nascent polypeptide at that point or readthrough and hence production of P1234. The opal termination codon is present at the nsP3/nsP4 junction of the alphaviruses SIN, AURA, WEE, EEE, VEE, and RR, and thus the P123 and P1234 species are expressed in cells infected with these viruses. In contrast, no termination codon is present at the nsP3/nsP4 junction of the alphaviruses SF and ONN, and thus only the P1234 species is expressed in cells infected with these viruses. Both the polyprotein and processed monomeric forms of the nonstructural proteins function in the replication of the alphavirus RNA genome. Translational readthrough generally occurs about 10%–20% of the time in cells infected with wild type Sindbis virus containing the opal termination codon at the nsP3/nsP4 junction. Processing of P123 and P1234 is by a proteinase activity encoded by the one of the nonstructural proteins, and is discussed further below. Each nonstructural protein has several functions, some of which are discussed in more detail within U.S. Pat. No. 5,843,723 and PCT Publication No. WO 97/38087.

4. Viral Junction Regions

The alphavirus viral junction region promoter normally controls transcription initiation of the subgenomic mRNA. Thus, this element also is referred to as the subgenomic mRNA promoter. In the case of Sindbis virus, the normal viral junction region typically begins at approximately nucleotide number 7579 and continues through at least nucleotide number 7612 (and possibly beyond). At a minimum, nucleotides 7579 to 7602 (5'-ATC TCT ACG GTG GTC CTA AAT AGT-SEQ. ID NO. 1) are believed necessary for transcription of the subgenomic fragment. This region (nucleotides 7579 to 7602) is hereinafter referred to as the "minimal junction region core." It is the complement of these junction region sequences, present in alphavirus minus strand RNA, that has functional promoter activity and allows for nsP-mediated transcription of subgenomic mRNA.

5. Alphavirus RNA Polymerase Recognition Sequence, Poly(A) Tract

As noted above, alphavirus vector constructs or RNA vector replicons of the present invention also should include an alphavirus RNA polymerase recognition sequence (also termed "alphavirus replicase recognition sequence", "3' terminal CSE", or "3' cis replication sequence"). Briefly, the alphavirus RNA polymerase recognition sequence, which is located at the 3' end region of positive stranded genomic RNA, provides a recognition site at which the virus begins replication by synthesis of the negative strand. A wide variety of sequences may be utilized as an alphavirus RNA polymerase recognition sequence. For example, within one embodiment, Sindbis virus vector constructs in which the polymerase recognition is truncated to the smallest region that can still function as a recognition sequence (e.g., nucleotides 11,684 to 11,703) can be utilized. Within another embodiment of the invention, Sindbis virus vector constructs in which the entire nontranslated region downstream from the glycoprotein E1 gene to the 3' end of the viral genome including the polymerase recognition site (e.g., nucleotides 11,382 to 11,703), can be utilized.

Within preferred embodiments of the invention, the alphavirus vector construct or RNA vector replicon may additionally contain a poly(A) tract. Briefly, the poly(A) tract may be of any size which is sufficient to promote recognition of the alphavirus 3' cis replication sequence by nonstructural proteins and stability in the cytoplasm, thereby increasing the efficiency of initiating the viral life cycle. Within various embodiments of the invention, the poly(A) tract comprises at least 25 adenosine nucleotides, and most preferably, at least 40 adenosine nucleotides. Within one embodiment, the poly(A) sequence is attached directly to Sindbis virus nucleotide 11,703.

C. Alphavirus Structural Polyprotein Genes

Wild-type alphavirus virions consist of four elements: a single-stranded genome RNA, repeating units of a capsid (C) protein monomer which interacts with the RNA to form an icosahedral nucleocapsid, a host-derived lipid bilayer (envelope), and two viral-encoded envelope glycoproteins, E1 and E2, which protrude as heterodimeric spikes. In addition, some alphavirus virions also contain another protein, E3. The alphavirus structural proteins are synthesized during virus replication as a single polyprotein from subgenomic RNA. The polyprotein (shown in FIG. 1), comprises the ordered elements C, E3, E2, 6K, E1, and proteolytic processing gives rise to the final protein products. E3 and 6K serve as signal peptides for insertion of glycoproteins E2 and E1, respectively, into the endoplasmic reticulum.

Figure 2:
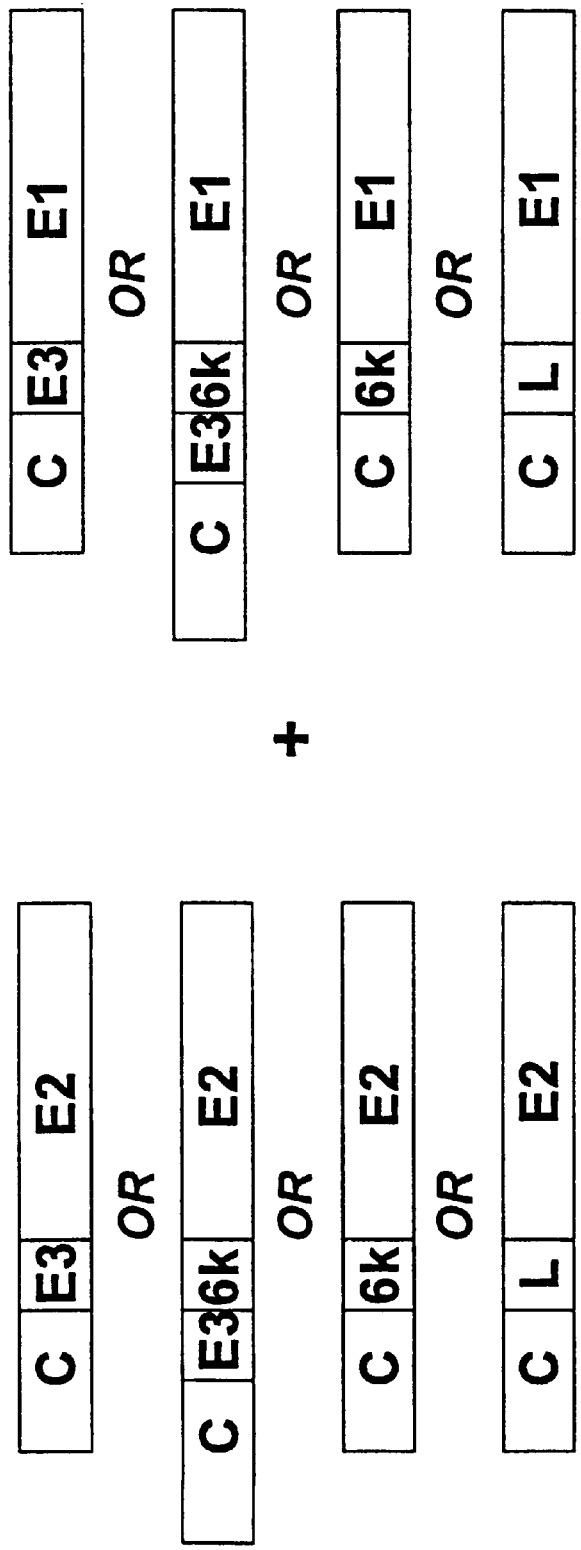
FIG. 2 is a schematic illustration of selected representative alphavirus structural polyproteins suitable for use in vector replicon RNA packaging.

Recombinant alphavirus vector particles are packaged using these same structural proteins as wild-type virions. In general, alphavirus vector RNA packaging has been performed by expressing in cells an intact, wild-type structural polyprotein which is maintains its ability to be processed into the individual protein species by normal mechanisms (FIG. 2). More recently, it was shown that the capsid protein and envelope glycoproteins could be expressed separately from separate cassettes and still result in functional packaging of vector (U.S. Pat. No. 5,789,245). In this configuration, a polyprotein comprising E3-E2-6K-E1, which maintains the wild-type virus gene order and processing, was utilized. The present invention provides alphavirus structural polyproteins significantly different from those previously described, and makes use altered gene order and both alphavirus and non-alphavirus derived leader/signal peptides for novel polyproteins (e.g., C-L-E1, C-6K-E1, C-E3-6K-E1, C-E3-E1, C-E3-E2, see FIG. 2). As discussed above, as well as in the examples below, the novel alphavirus structural polyproteins provide certain advantages when used for packaging vectors.

D. Expression Cassettes Containing Alphavirus Structural Polyprotein Genes

Within one aspect of the invention, a variety of expression cassettes are provided, which contain the sequences coding for and operably express one or more alphavirus structural polypeptides provided herein. Generally, the expression cassettes fall within one of three categories: 1) a DNA promoter of RNA transcription (e.g., RNA polymerase II promoter) directly and operably linked to the structural protein open reading frame (ORF), and a transcription termination/polyadenylation sequence; 2) an alphavirus defective helper RNA transcribed in vitro or in vivo, comprising the ordered elements 5' viral or defective-interfering RNA sequence required in cis for alphaviral replication (also referred to as 5' CSE, in background), viral subgenomic junction region promoter, alphavirus structural protein sequence of the present invention, 3' alphaviral sequence required in cis for replication (also referred to as 3' CSE, in background), and polyadenylate tract; and 3) DNA cassettes comprising the ordered elements of a DNA promoter of RNA transcription that functions within a eukaryotic cell (e.g., RNA polymerase II promoter) and is operably linked to a 5' viral or defective-interfering RNA sequence required in cis for alphaviral replication, viral subgenomic junction region promoter, alphavirus structural protein sequence of the present invention, 3' alphaviral sequence required in cis for replication, polyadenylate tract, and transcription termination/polyadenylation sequence. In preferred embodiments, the structural proteins of the present invention are synthesized at high levels by the cassettes only after induction by the RNA vector replicon itself or some other provided stimulus.

E. Alphavirus Packaging Cell Lines

Within further aspects of the invention, alphavirus packaging cell lines are provided. In particular, within one aspect of the present invention, alphavirus packaging cell lines are provided wherein the viral structural proteins are supplied in trans from one or more stably transformed expression cassettes, and are able to encapsidate transfected, transduced, or intracellularly produced alphavirus vector RNA transcripts in the cytoplasm and release infectious packaged vector particles through the plasma membrane. In preferred embodiments, the structural proteins necessary for packaging are synthesized at high levels only after induction by the RNA vector replicon itself or some other provided stimulus, and the transcripts encoding these structural proteins are capable of cytoplasmic amplification in a manner that will allow expression levels sufficient to mimic that of a natural viral infection (WO 97/38087 and U.S. Pat. No. 5,789,245). Furthermore, in other embodiments, expression of a selectable marker is operably linked to the structural protein expression cassette. Such a linked selectable marker allows efficient generation of functional, stably transformed packaging cell lines.

F. Methods of Packaging Recombinant Alphavirus Particles

As provided by the invention, generation (packaging) of recombinant alphavirus vector particles may be readily accomplished by, for example, co-transfection of complementing vector and defective helper (DH) molecules derived from in vitro transcribed RNA, or plasmid DNA, or by co-infection with virus (see Bredenbeek et al., *J. Virol.* 67:6439–6446, 1993, Dubensky et al., *J. Virol* 70:508–519, 1996 and U.S. Pat. Nos. 5,814,482, 5,739,026, 5,766,602, 5,789,245 and 5,792,462. Alternatively, vector particles may be generated by introduction of vector RNA into stable alphavirus packaging cell lines (PCL, U.S. Pat. No. 5,789,245). Briefly, such PCL and their stably transformed structural protein expression cassettes can be derived using methods described within U.S. Pat. No. 5,789,245, or using novel methods described within this invention. For example, the production of recombinant alphavirus vector particles by PCL may be accomplished following introduction of alphavirus-based vector molecules into the PCL, the vectors being derived from in vitro transcribed RNA, plasmid DNA, or previously obtained recombinant alphavirus particles, incubating the PCL for a under conditions and for a time necessary for vector particle packaging, and harvesting of the packaged vector particles. As shown in the detailed examples provided herein, utilization of the novel alphavirus structural polyproteins of the present invention for efficient vector packaging in such approaches is readily accomplished.

G. Methods of Reducing Heterologous Gene Expression During Packaging

Also provided in the invention are methods to reduce expression of a heterologous sequence (also referred to as a "transgene") from an alphavirus vector during the production of recombinant alphavirus vector particles (e.g., packaging of vector RNA). Such methods are advantageous given the very high level expression of transgene in cells during vector packaging and the often deleterious effects of transgene expression on final vector particle titer due to interference with glycoprotein transport and processing, competition with alphavirus gene product function, and general toxicity for the host or packaging cell. Reduction of transgene expression during vector packaging provides one mechanism to addresses these issues. In preferred embodiments, the level of heterologous transgene expression in cells used for packaging is reduced at least 25%, 50%, 75%, 95%, or, 3-fold, 5-fold, 10-fold, or even about 100-fold as compared to the level of expression in a target cell.

The approaches provided herein to reduce expression of a transgene in alphavirus vectors are directed at the reduction of transcription or translation of the vector subgenomic RNA. Such approaches are deemed necessary because reduction in the overall ability of the vector itself to replicate would have an adverse effect of the production of alphavirus vector particles.

In one embodiment, a method of producing alphavirus vector particles is provided, comprising introducing into a population of cells (a) an alphavirus vector construct or vector RNA replicon, (b) an alphavirus structural protein expression cassette described herein encoding capsid and glycoprotein E2, and (c) an alphavirus structural protein expression cassette described herein encoding capsid and glycoprotein E1, such that recombinant alphavirus particles are produced, wherein the cells contain a cassette which expresses an RNA sequence complementary to (e.g., antisense) the junction region promoter or subgenomic RNA of the alphavirus vector RNA. The antisense sequence may be operably linked to and expressed directly from a eukaryotic promoter (e.g., RNA polymerase I, II, or III promoter), or it may be expressed from an alphavirus junction region promoter, such as in the various cassettes (e.g., defective helper RNA) provided herein. In those instances where it is expressed from an alphavirus junction region promoter, sufficient sequence differences should be included to prevent binding of the antisense RNA to its own junction region promoter or 5'-end. In addition, antisense RNA molecules of the present invention may be complementary to any sequence of the subgenomic RNA, but preferably the antisense RNA is complementary to a sequence at or near the 5'-nontranslated region or AUG initiation codon of the subgenomic RNA. In preferred embodiments, the cells that contain a cassette that expresses an antisense RNA of the present invention are stably transformed with said cassette.

In another embodiment, a method of producing alphavirus vector particles is provided, comprising introducing into a population of cells (a) an alphavirus vector construct or vector RNA replicon, (b) an alphavirus structural protein expression cassette described herein encoding capsid and glycoprotein E2, and (c) an alphavirus structural protein expression cassette described herein encoding capsid and glycoprotein E1, such that recombinant alphavirus particles are produced, wherein the alphavirus vector construct or vector RNA replicon further comprises an RNA aptamer sequence that binds to a ligand provided, therein reducing translation from the subgenomic RNA, said RNA aptamer being inserted within the vector sequence corresponding to said subgenomic RNA. The RNA aptamer sequence used in methods of the present invention is not limited to those explicitly described herein. Rather, any RNA aptamer with a known binding ligand may be readily substituted by one of skill in the are, using this disclosure. In utilizing an RNA aptamer and ligand binding pair, it is preferable to choose an aptamer and site for insertion into the vector that does not interfere with replication of the alphavirus vector or with translation of the subgenomic mRNA in the absence of its ligand. In preferred embodiments, the RNA aptamer within the alphavirus vector construct or vector RNA replicon binds to a ligand that is an antibiotic, such as Tobramycin or Kanamycin. In another preferred embodiment, the RNA aptamer within the alphavirus vector construct or vector RNA replicon binds to Hoechst dyes H33258 or H33342 (Werstuck and Green, 1998, *Science* 282:296–298). In particularly preferred embodiments, the RNA aptamer is inserted within the 5'-nontranslated region of the alphavirus subgenomic RNA.

H. Heterologous Sequences

As briefly noted above, a wide variety of heterologous sequences may be included within the alphavirus vectors described herein including, for example, sequences which encode palliatives such as lymphokines or cytokines, toxins, and prodrug converting enzyme, sequences which encode antigens that stimulate an immune response, ribozymes or antisense sequences, sequences which encode proteins for therapeutic application such as growth or regulatory factors, and sequences which encode proteins that assist or inhibit an immune response.

Preferably, the nucleotide sequences should be of a size sufficient to allow efficient production of viable vector particles. Within the context of the present invention, the production of any measurable titer of recombinant alphavirus particles, for example, by transfer of expression assay, titering cell line assay, reporter assay, or plaque assay on appropriate susceptible monolayers, is considered to be "production of viable vector particles". This may be, at a minimum, an alphavirus vector construct which does not contain any additional heterologous sequence. However, within other embodiments, the vector construct may contain additional heterologous or foreign sequences. Within preferred embodiments, the heterologous sequence can comprise a heterologous sequence of at least about 100 bases, 2 kb, 3.5 kb, 5 kb, 7 kb, or even a heterologous sequence of at least about 8 kb. The above-described heterologous sequences may be readily obtained from a variety of sources, including for example, depositories such as the American Type Culture Collection (ATCC, Rockville, Md.), or from commercial sources such as British Bio-Technology Limited (Cowley, Oxford, England). Alternatively, cDNA sequences which encode the above-described heterologous sequences may be obtained from cells which express or contain the sequences, utilizing standard procedures known in the art. In addition, heterologous sequences also may be synthesized, for example, on an Applied Biosystems, Inc. DNA synthesizer.

Representative examples of suitable heterologous sequences are discussed in more detail within U.S. Pat. No. 5,843,723 and PCT Publication No. WO 97/38087.

The following examples are included to more fully illustrate the present invention. Additionally, these examples provide preferred embodiments of the invention and are not meant to limit the scope thereof. Standard methods for many of the procedures described in the following examples, or suitable alternative procedures, are provided in widely reorganized manuals of molecular biology, such as, for example, "Molecular Cloning," Second Edition (Sambrook et al., Cold Spring Harbor Laboratory Press, 1987) and "Current Protocols in Molecular Biology" (Ausubel et al., eds. Greene Associates/Wiley Interscience, NY, 1990).

EXAMPLE 1

Construction of the C-E3-E2 Structural Polyprotein and Cassette

The C-E3-E2 polyprotein and expression cassette comprises the coding regions for an alphavirus capsid protein and glycoprotein E2. As described above, a leader/signal sequence also is included to facilitate insertion of the envelope glycoprotein into the endoplasmic reticulum. As will be evident from the examples provided herein, a variety of alphavirus (e.g., E3, 6k) or non-alphavirus (e.g., TPA) leader/signal sequences may be incorporated as part of the polyprotein open reading frame. For example, one version of the cassette comprises C-E3-E2 and was assembled by PCR amplification to include the insertion of a stop codon after the final amino acid (aa806) of E2. Specifically, PCR was performed with the following primers:

XCAPSIDF:
5'CTC GAG ACC ATG AAT AGA GGA TTC TTT AAC (SEQ. ID NO. 2)
NGLYCOE2R:
5'GCG GCC GCT CAA GCA TTG GCC GAC CTA ACG CAG CAC (SEQ. ID NO. 3)

The capsid forward primer (XCAPSIDF) contained a XhoI site to facilitate subcloning, a Kozak consensus sequence, and the first twenty one bases of the capsid open reading frame (ORF). The E2 reverse primer (NGLYCOE2R) contained a NotI site to facilitate subcloning, a UGA stop codon, and the last 25 bases of the glycoprotein E2 ORF.

PCR amplification was performed using PFU polymerase (Stratagene Inc., San Diego, Calif.) as per the manufacturer's instructions. The PCR template was the CMV Promoter driven Sindbis virus genomic clone pDCMVSINg (Dubensky et al., 1996, *J. Virol.* 70:508–519). The PCR reaction was cycled 20×(95° C. 30 sec, 60° C. 30 sec, 72° C. 4 min), and the PCR product and corresponding polyprotein referred to as C-E3-E2 (FIG. 2).

Figure 3:
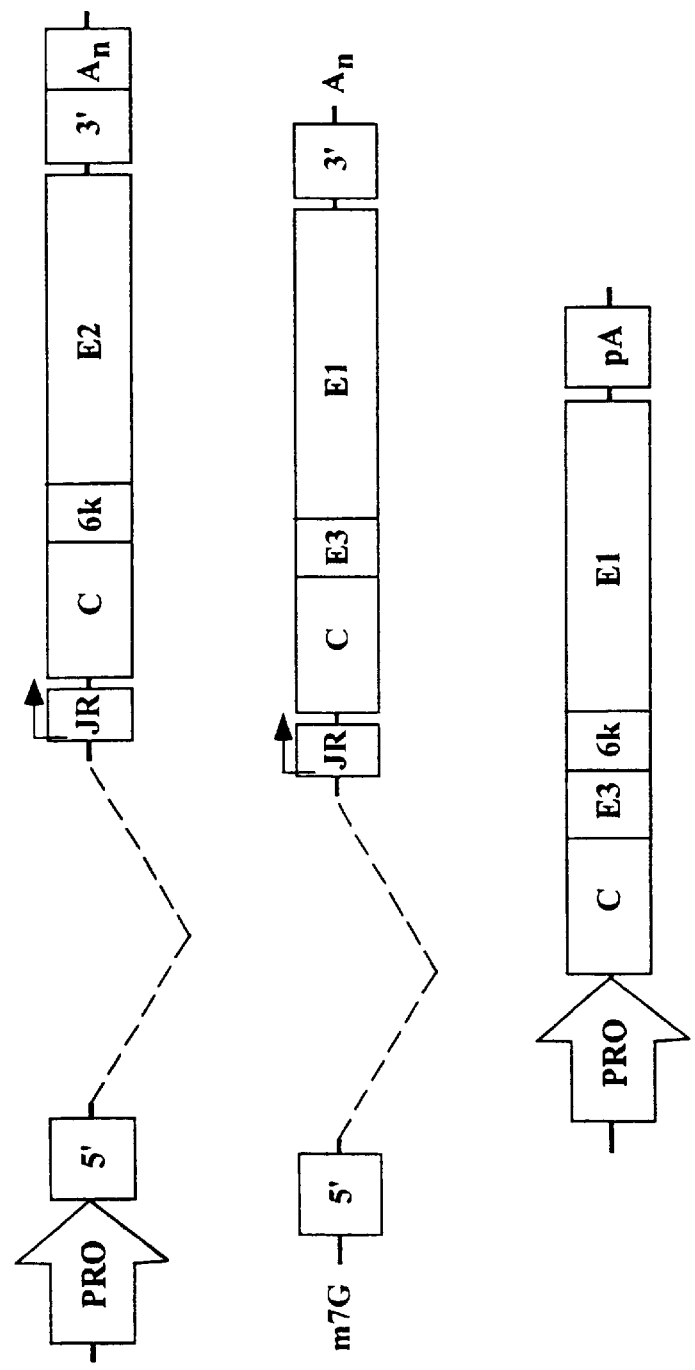
FIG. 3 is a schematic illustration of representative expression cassettes used for expression of alphavirus structural polyproteins of the present invention and packaging of vector replicon RNA.

The 2.3 kbp C-E3-E2 PCR product was cloned into the pCR-Blunt vector using the Zero Blunt PCR Cloning Kit (Invitrogen, Inc. Carlsbad, Calif.) as per the manufacturer's instructions. Plasmid DNA was isolated and screened for the presence of the PCR insert by digestion with XhoI and NotI restriction endonucleases. The C-E3-E2 fragment was isolated from pCR-Blunt by digestion with XhoI and NotI, purification from a 1% agarose gel using the GeneCleanII kit (GENECLEAN, Bio 101 Inc., Vista, Calif.) as per the manufacturer's instructions, and inserted into appropriate expression cassettes (FIG. 3) as described below.

Construction of a C-E3-E2 expression cassette was performed by insertion of the isolated C-E3-E2 fragment into a Sindbis virus derived defective helper configuration, comprising the following ordered elements: a 5' sequence which initiates transcription of alphavirus RNA from viral RNA, a viral subgenomic junction region promoter, an alphavirus polyprotein gene described herein, an alphavirus RNA polymerase recognition sequence, and a polyadenylate tract. In this example, the defective helper is a cDNA contained within a plasmid, wherein the defective helper is operably linked to a bacteriophage (e.g., SP6) promoter for in vitro transcription, and also contains a unique restriction site downstream of the polyadenylate tract for linearization of the plasmid. Specifically, the defective helper plasmid was constructed by modification of the previously described Sindbis virus vector pRSIN-luc (Dubensky et al., 1996, ibid). Plasmid pRSIN-luc was digested with BspEI to remove most Sindbis virus nonstructural protein gene sequences and the vector was then re-ligated to itself, resulting in a construct referred to as pRSINdl-luc. This plasmid was next digested with NotI and SacI to remove the minimal Sindbis 3'-end sequence and $A_{25}$ tract, which were replaced with an approximately 0.4 kbp fragment from pKSSIN1-BV (WO 97/38087) containing the complete Sindbis virus 3'-end, an $A_{40}$ tract and a PmeI site for linearization prior to transcription, obtained from pKSSIN1-BV after digestion with NotI and SacI, and purification from an agarose gel. This new construct was designated SINdl-luc. Plasmid SINdl-luc was digested with XhoI and NotI to remove the luciferase gene insert and the remaining vector portion was purified from an agarose gel using GENECLEAN. The isolated C-E3-E2 fragment (from above) was then ligated into the vector, resulting in the expression construct SINdl-CE3E2.

EXAMPLE 2

Construction of the C-E3-6K-E1 Structural Polyprotein and Cassette

This polyprotein and expression cassette comprises the coding regions for an alphavirus capsid protein and glycoprotein E1. As described above, a leader/signal sequence also is included to facilitate insertion of the envelope glycoprotein into the endoplasmic reticulum. For example, one version of the cassette comprises C-E3-6K-E1 (FIG. 2) and was assembled by using two separate PCR amplification reactions for C-E3 and 6K-E1. Specifically, a C-E3 PCR product was generated with the following primers:
XCAPSIDF:
5'CTC GAG ACC ATG AAT AGA GGA TTC TTT AAC (SEQ. ID NO. 2)
BE3R:
5'GGA TCC GTC GTC AAC GAC GCT TCT TTT GC (SEQ. ID NO. 4)
The capsid forward primer (XCAPSIDF) was described above. The E3 reverse primer (BE3R) contains a BamHI site to facilitate subcloning. The PCR reaction and subsequent subcloning into pCR-Blunt was performed as described above, using the Sindbis virus genomic clone pDCMVSINg (Dubensky et al., ibid) as template. Clones were screened with the restriction endonucleases XhoI and BamHI, the plasmid then digested with XhoI and BamHI, and the 1 kbp C-E3 fragment purified from an agarose gel using GeneCleanII. This fragment was subcloned into XhoI/BamHI digested pBluescript-KS plasmid (Stratagene Inc.), resulting in a plasmid called pKS-C-E3.

The 6K-E1 PCR product was generated with the following primers:
B6KF:
5'GGA TCC AGG TCG GCC AAT GCT GAA ACG TTC ACC GAG ACC ATG AGT TAC (SEQ. ID NO. 5)
NEIR:
5'GCG GCC GCT CAT CTT CGT GTG CTA GTC AGC ATC (SEQ. ID NO. 6)
The B6KF forward primer contains a BamHI site and the NEIR reverse primer contains a NotI site to facilitate subcloning. The PCR reaction and subsequent subcloning into pCR-Blunt was performed as described above, using the Sindbis virus genomic clone pDCMVSINg (Dubensky et al., ibid) as template. Clones were screened with the restriction endonucleases BamHI and NotI, the plasmid then was digested with BamHI and NotI, and the 1.5 kbp C-E3 fragment purified from an agarose gel using GeneCleanII. This fragment was subcloned into BamHI/NotI digested pKS-C-E3 plasmid, resulting in the new plasmid called pKS-C-E3-6K-E1.

The C-E3-6K-E1 fragment was isolated by digestion with XhoI and NotI, purified from a 1% agarose gel using GENECLEAN, and ligated into SINdl-luc that also was digested with XhoI and NotI to remove the luciferase gene insert (as described above). The resulting expression construct was designated SINdl-CE36KE1.

EXAMPLE 3

Construction of the C-6K-E1 Structural Polyprotein and Cassette

This polyprotein and expression cassette comprises the coding regions for an alphavirus capsid protein and glycoprotein E1. As described above, a leader/signal sequence also is included to facilitate insertion of the envelope glycoprotein into the endoplasmic reticulum. For example, one version of the cassette comprises C-6K-E1 (FIG. 2) and was assembled by using two separate PCR amplification reactions for C-6K and 6K-E1, followed by an overlapping PCR reaction. The last two codons of E3 are retained to preserve the capsid protease cleavage site. Specifically, a C-6K PCR product was generated with the following primers:
XCAPSIDF:
5'CTC GAG ACC ATG AAT AGA GGA TTC TTT AAC (SEQ. ID NO. 2)
6KE3CR:
5'CTC GGT GAA CGT TTC TGC GGA CCA CTC TTC TGT CCC TTC (SEQ. ID NO. 7)
The capsid forward primer (XCAPSIDF) was described above. The 6K reverse primer (BE3R) contains the last six codons of capsid, the first two codons of E3, and the first six codons of 6K. The resulting 0.8 kbp PCR product contains: 5'XhoI site/capsid ORF/first two codons of E3/first five codons of 6K.

In the other reaction, a 6K-E1 PCR product was generated with the following primers:
CE36KF:
5'GAA GAG TGG TCC GCA GAA ACG TTC ACC GAG ACC ATG AG (SEQ. ID NO. 8)
NE1R:
5'GCG GCC GCT CAT CTT CGT GTG CTA GTC AGC ATC (SEQ. ID NO. 6)
The 6K forward primer (CE36KF) contains the last three codons of capsid, the first two codons of E3, and the first twenty-three nucleotides of the 6K ORF. The NE1R primer was described previously. The resulting 1.5 kbp PCR product contains: 5' last three codons of capsid/first two codons of E3/6K ORF/E1 ORF/NotI site.

Both PCR reactions were performed as above using pDCMVSINg as template. The separate PCR products were purified from an agarose gel using GeneCleanII, and then combined as template for an "overlapping" PCR reaction containing the primers XCAPSIDF and NEIR. The resulting 2.3 kbp C-6K-E1 fragment was then gel purified, subcloned into pCR-Blunt, and screened with XhoI and NotI to identify the new construct pCR-Blunt-C-6K-E1.

The C-6K-E1 fragment was isolated from pCR-Blunt-C-6K-E1 by digestion with XhoI and NotI, purified from a 1% agarose gel using GENECLEAN, and ligated into SINdl-luc that also was digested with XhoI and NotI to remove the luciferase gene insert (as described above). The resulting expression construct was designated SINdl-C6KE1.

EXAMPLE 4

Construction of the C-E3-E1 Structrual Polyprotein and Cassette

This polyprotein and expression cassette comprises the coding regions for an alphavirus capsid protein and glycoprotein E1. As described above, a leader/signal sequence also is included to facilitate insertion of the envelope glycoprotein into the endoplasmic reticulum. For example, one version of the cassette comprises C-E3-E1 (FIG. 2) and was assembled by using two separate PCR amplification reactions for C-E3 and E3-E1, followed by an overlapping PCR reaction. Specifically, a C-E3 PCR product was generated with the following primers:
SINCAPF:
5'ATATATCTCGAGCACCATGAATAGAG-GATTCTTTAAC (SEQ. ID NO. 9)
CE3E1R:
5'GTGGTCGCATGTTCGCTTCTTTTGCT-TCTGCCAGACG (SEQ. ID NO. 10)

The capsid forward primer (SINCAPF) contains a XhoI site to facilitate subcloning and the structural polyprotein Kozak consensus sequence. The E3 reverse primer (CE3E1R) contains the last six codons of E3, a serine codon in place of the first E1 codon, and the next four codons of E1. The resulting 1 kbp PCR product contains: 5'XhoI site/capsid ORF/E3 OFR/SER codon/first four codons of E1.

In the other reaction, an E3-E1 PCR product was generated with the following primers:
E3E1F:
5'GAAGCAAAAGAAGCGAACATGCGAC-CACTGTTCCAAATG (SEQ. ID NO. 11)
SINE1R:
5'TATATAGCGGCCGCTCATCTTCGTGT-GCTAGTCAGCATC (SEQ. ID NO. 12)

The E3 forward primer (E3E1F) contains the last four codons of E3, a serine codon in place of the first E1 codon, and the first 8 codons of the E1 ORF. The E1 reverse primer (SINE1R) contains a NotI site to facilitate subcloning. The resulting 1.3 kbp PCR product contains: 5' last four codons of E3/SER codon/E1 ORF/NotI site.

Both PCR reactions were performed as above using the Sindbis virus genomic pDCMVSINg as template. The separate PCR products were purified using QIAquick PCR purification kit (QIAGEN, Santa Clarita, Calif.), and then combined as template for an "overlapping" PCR reaction containing the primers SINCAPF and SINE1R. The resulting 2.3 kbp C-E3-E1 PCR product was purified using the QIAquick kit, digested with XhoI and NotI, and isolated from an agarose gel using GENECLEAN. This isolated C-E3-E1 PCR fragment was then cloned directly into SINdl-luc that also was digested with XhoI and NotI to remove the luciferase gene insert (as described above). The resulting expression construct was designated SINdl-CE3E1.

EXAMPLE 5

Construction of the C-TPA-E1 Structural Polyprotein and Cassette

This polyprotein and expression cassette comprises the coding regions for an alphavirus capsid protein and glycoprotein E1. As described above, a leader/signal sequence also is included to facilitate insertion of the envelope glycoprotein into the endoplasmic reticulum. For example, one version of the cassette utilizes a non-alphavirus derived leader/signal peptide sequence, such as that of tissue plasminogen activator (TPA), and comprises the polyprotein C-leader-E1 (FIG. 2). For use of the TPA leader, this construct is assembled by using two separate PCR amplification reactions for C-TPA and TPA-E1, followed by an overlapping PCR reaction. Specifically, a C-TPA PCR product is generated with the following primers:
SINCAPF:
5'ATATATCTCGAGCACCATGAATAGAG-GATTCTTTAAC (SEQ. ID NO. 9)
TPACAPR:
5'TGCTCCACACAGCAGCAGCACACAGCA-GAGCCCTCTCTTCATTGCATCTGCGGAC-CACTCTTCTGTCCCTTCCGG (SEQ. ID NO. 13)

The capsid forward primer (SINCAPF) was described above. The TPA reverse primer (TPACAPR) contains the last seven codons of capsid, the first two codons of E3, and the first 16 codons of TPA leader. The resulting 0.9 kbp PCR product contains: 5'XhoI site/capsid ORF/TPA ORF.

In the other reaction, a TPA-E1 PCR product was generated with the following primers:
TPAE1F:
5'TGTGTGCTGCTGCTGTGTGGAGCAGTCT-TCGTTTCGCCCAGCGCTAGCTACGAA-CATGCGACCACTGTTCCAAAT (SEQ. ID NO. 14)
SINE1R:
5'TATATAGCGGCCGCTCATCTTCGTGT-GCTAGTCAGCATC (SEQ. ID NO. 12)

The TPA forward primer (TPAE1F) contains the last 16 codons of TPA, including the cleavage signal, and the first nine codons of the E1 ORF. The E1 reverse primer (SINE1R) was described above. The resulting 1.4 kbp PCR product contains: 5' last 16 codons of TPA/E1 ORF/NotI site.

Both PCR reactions were performed as above using the Sindbis virus genomic pDCMVSINg as template. The separate PCR products were purified using the GENECLEAN II Kit and then combined as template for an "overlapping" PCR reaction containing the primers SINCAPF and SINE1R. The resulting 2.3 kbp C-TPA-E1 PCR product was purified using the QIAquick kit, digested with XhoI and NotI, and isolated from an agarose gel using GENECLEAN. This isolated C-TPA-E1 PCR fragment was then cloned directly into SINdl-luc that also was digested with XhoI and NotI to remove the luciferase gene insert (as described above). The resulting expression construct was designated SINdl-CTPAE1.

Similarly to that described above, a non-alphavirus leader (e.g., TPA) also may be used to generate polyproteins and expression cassettes with an alphavirus E2 glycoprotein.

EXAMPLE 6

Vector Packaging with Structural Polyprotein Expression Cassettes

Figure 4:
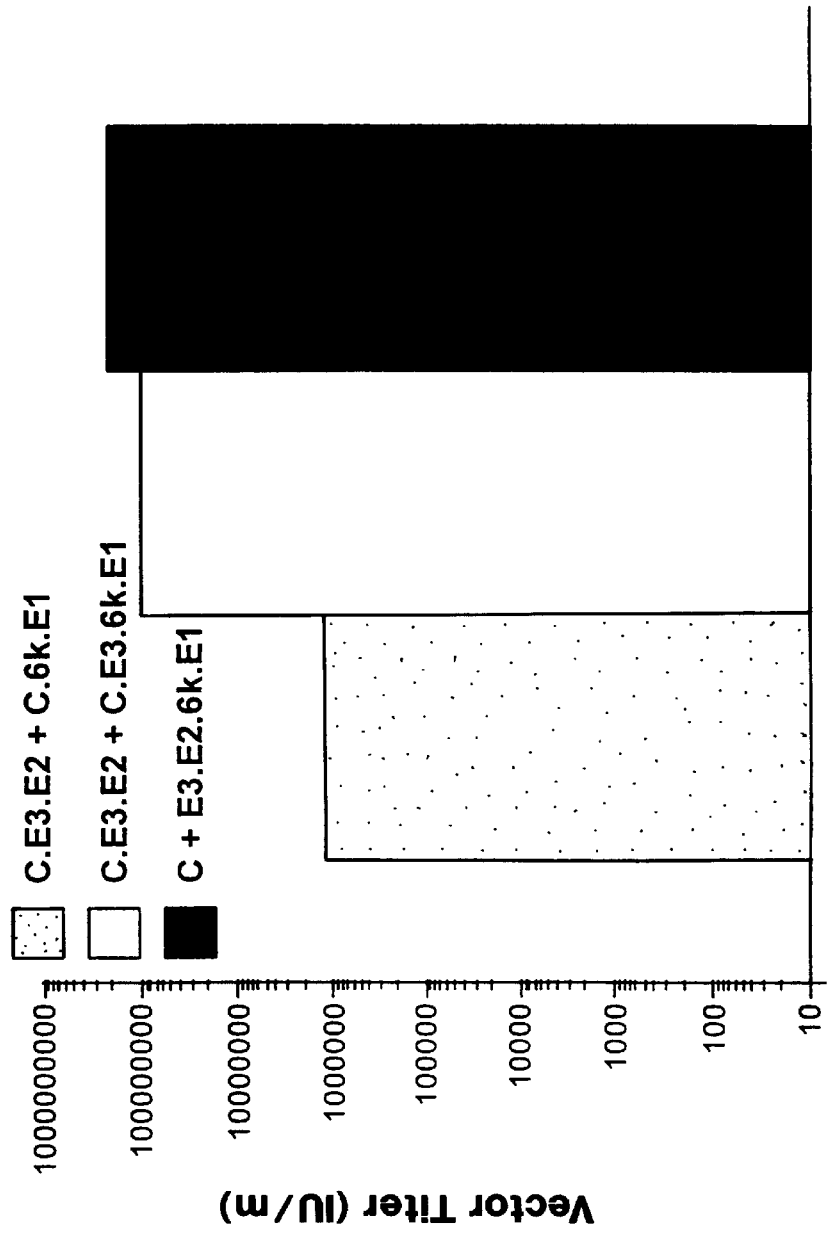
FIG. 4 is a graph demonstrating alphavirus vector packaging using representative structural polyprotein cassettes of the present invention.
Figure 5:
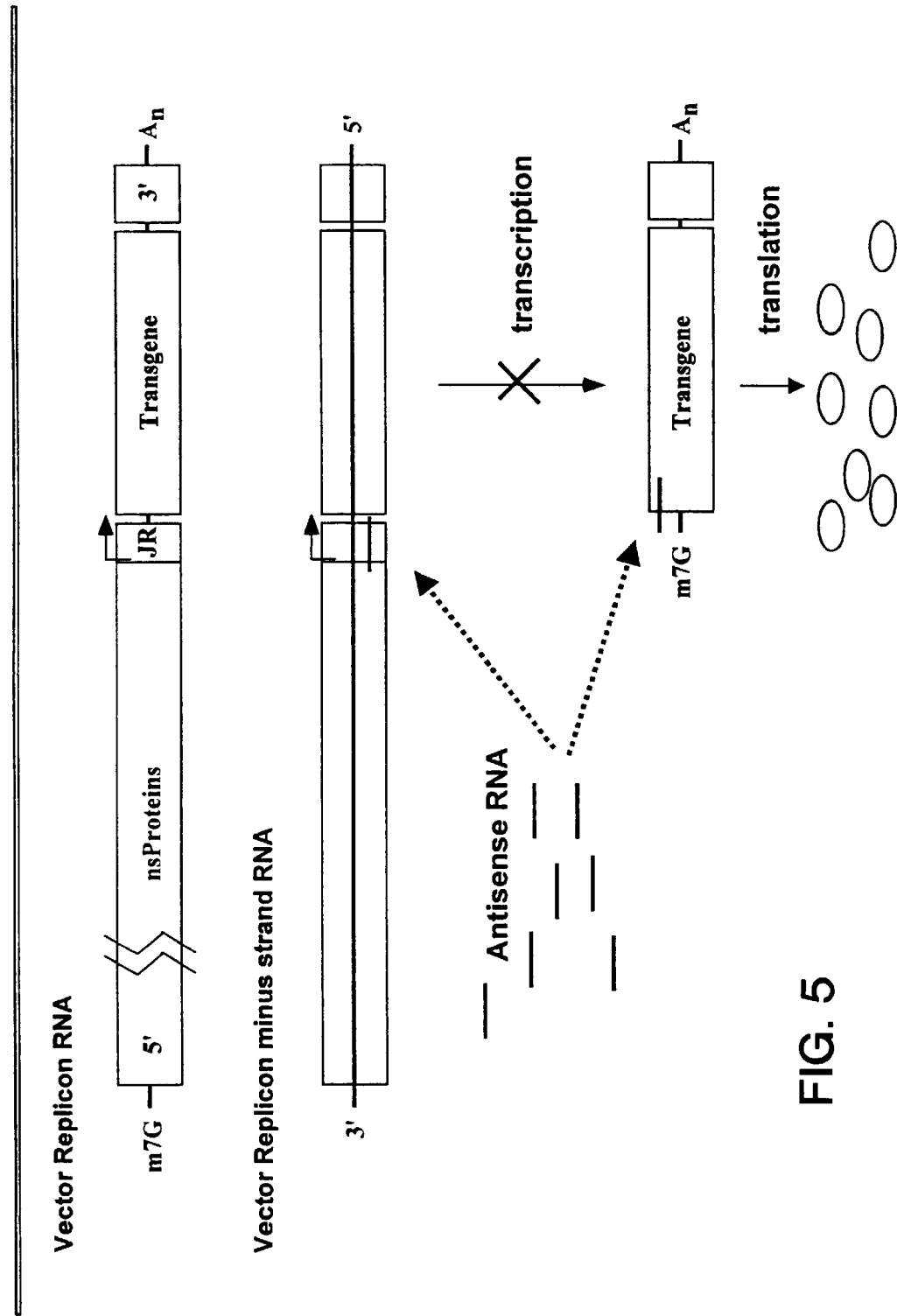
FIG. 5 is a schematic illustration of two representative methods for reducing heterologous transgene expression from alphavirus vectors using antisense RNA.

Packaging of alphavirus vectors with various combinations of the above structural protein expression cassettes was demonstrated using, as an example, Sindbis vector replicons expressing a β-galactosidase or GFP reporter (Dubensky et al., 1996, ibid; Polo et al., 1999, *PNAS* 96:4598–4603). The SIN vector was linearized as described previously, and the various structural protein expression cassettes also were linearized using PmeI. Vector and defective helper RNAs then were transcribed in vitro from the linearized plasmids, with bacteriophage SP6 polymerase as described in Dubensky et al. (ibid). To package vector particles, the SIN vector RNA was co-transfected into BHK-21 cells (Dubensky, ibid) together with the C-E3-E2 defective helper RNA and one of the E1 expressing defective helper RNAs, selected from the group C-6K-E1, C-E3-6K-E1, C-E3-E1, C-tPA-E1. Transfected cells were incubated at 37° C. for 24 hr, at which time the culture supernatants were harvested and clarified by centrifugation. Clarified supernatants were then serially diluted and used to infect in duplicate, naïve BHK-21 cells for approximately 14 hr. The infected cells were analyzed for reporter expression and the number of cells exhibiting such expression counted to determine vector particle titer in the original supernatants. Results demonstrating functionality of different E1 expressing constructs for vector packaging are shown in FIG. 4.

EXAMPLE 7

Derivation of Stable Alphavirus Vector Packaging Cell Lines

Stable alphavirus vector packaging cell lines that express the structural polyproteins of the present invention are generated using expression cassettes that function directly in eukaryotic cells, to stably transform an appropriate cell type (e.g., BHK-21, CHO cells), rather than requiring a prior step of in vitro transcription. The expression cassettes may comprise a DNA promoter of RNA synthesis (e.g., RNA polymerase II promoter) operably linked directly to the structural polyprotein genes, or a configuration wherein the structural polyprotein genes are operably linked to their native subgenomic promoter and require induction by vector supplied replicase (e.g., alphavirus nonstructural proteins, see U.S. Pat. No. 5,789,245). For example, cassettes expressing either Sindbis virus-derived polyproteins C-E3-E2 and C-E3-6K-E1 are constructed in a configuration comprising the following ordered elements: RNA polymerase II promoter, 5' viral or defective-interfering RNA sequence required in cis for alphaviral replication, viral subgenomic junction region promoter, alphavirus structural polyprotein sequence, 3' alphaviral sequence required in cis for replication, polyadenylate tract, and transcription termination sequence.

As a first step, an expression cassette backbone for use in packaging cells was constructed. This backbone can serve as the initial starting material for any of the structural polyprotein genes of the present invention. All components used in this construction have been described in detail previously (WO 97/38087). Specifically, the expression cassette backbone was generated by step-wise insertions into plasmid pBGSV3'. A Sindbis virus junction region promoter plus XhoI and NotI cloning sites were obtained as a luciferase reporter-containing fragment from plasmid pDCMVSIN-luc, by digestion with BamHI and FspI, and purification of the luciferase reporter-containing fragment from a 0.7% agarose gel using GENECLEAN. The fragment was ligated into plasmid pBGSV 3'that also had been digested with BamHI and FspI, and treated with alkaline phosphatase to produce a plasmid designated pBGSV3'BaFLuc. Next, an RSV (polII) promoter/5'-end tRNA sequence was obtained from 987DHBB by digestion with BglII and BamHI and purification from a 1% agarose gel using GENECLEAN. This fragment was ligated into pBGSV3'BaFLuc that was similarly digested with BglII and BamHI, to produce the expression cassette backbone construct pBRSV987dl-Luc. Alphavirus structural polyprotein genes and selectable markers are next inserted into this cassette in appropriate combinations.

The C-E3-E2 polyprotein gene is obtained from plasmid SINdl-CE3E2 (Example 1) by digestion with XhoI and NotI, and purification from an agarose gel using GENECLEAN. The C-E3-E2 fragment is then ligated into the packaging cell line expression plasmid, pBRSV987dl-Luc, which is also digested with XhoI and NotI to remove the luciferase gene insert, and purified from an agarose gel using GENECLEAN. The resulting construct is designated pBRSV987dl-CE3E2. Insertion of a neomycin phosphotransferase gene ($neo^R$) into the region of nonstructural protein gene deletion as a selectable marker, is next accomplished by digestion with BspEI and BamHI, purification from an agarose gel using GENECLEAN, and ligation with a PCR-amplified $neo^r$ gene (see WO 97/38087) that is also digested with BspEI and BamHI, and purified from an agarose gel. The resulting construct is designated pBRSV987dlneo-CE3E2.

The C-E3-6K-E1 polyprotein gene is obtained from plasmid SINdl-CE36KE1 (Example 2) by digestion with XhoI and NotI, and purification from an agarose gel using GENECLEAN. The C-E3-6K-E1 fragment is then ligated into the packaging cell line expression plasmid pBRSV987dl-Luc, which is also digested with XhoI and NotI to remove the luciferase gene insert, and purified from an agarose gel using GENECLEAN. The resulting construct is designated pBRSV987dl-CE36KE1. Insertion of a hygromycin phosphotransferase gene ($hyg^r$) into the region of nonstructural protein gene deletion as a selectable marker is next accomplished by digestion with BspEI, blunt-ending with Klenow, and further digesting with BamHI. The $hyg^r$ insert is obtained as a PCR-amplified product (see WO 97/38087) digested with EcoRV and BamHI, and purified from an agarose gel. This fragment is ligated into the prepared pBRSV987dl-CE36KE1 vector, resulting in the construct pBRSV987dlhyg-CE36KE1.

To generate stable alphavirus packaging cell lines, cells (e.g., BHK-21) are transfected initially with plasmid pBRSV98dlneo-CE3E2 using Lipofectamine, as described by the manufacturer. Approximately 24 hr post-transfection, the cells are trypsinized and re-plated in media containing 600 ug/ml of the drug G418 (neomycin). The media is exchanged periodically with fresh G418-containing media and foci of resistant cells are allowed to grow. Cells are trypsinized and cloned by limiting dilution in 96 well tissue culture dishes, and individual cell clones are grown and expanded for screening. Cells which inducibly expressed capsid protein and glycoprotein E2 in response to input vector are identified by transfecting with Sindbis luciferase vector RNA or Sindbis β-galactosidase DNA vectors (Dubensky et al., 1996, ibid), making cell lysates approximately 24 or 48 hr post-transfection, and performing western blot analysis with a rabbit anti-Sindbis polyclonal antibody. A positive CE3E2 cell line demonstrating expression of the Sindbis virus capsid and E2 is then used for subsequent steps.

Next, the positive CE3E2 cell line is transfected with pBRSV987dlhyg-CE36KE1 using Lipofectamine, as described by the manufacturer. Approximately 24 hr post-transfection, the cells are trypsinized and re-plated in media containing 500 ug/ml of hygromycin (Boehringer Mannheim). The media is exchanged periodically with fresh media containing hygromycin and foci of resistant cells are allowed to grow. Cells are trypsinized and cloned by limiting dilution in 96 well tissue culture dishes, and individual cell clones grown and expanded for screening. Split structural gene PCL derived in this manner are designated CE2/CE1 PCL. Positive cells which inducibly express all Sindbis virus structural proteins in a biologically active form in response to input vector are identified in transfer of expression (TOE) assays, which demonstrate that transfected vector molecules could induce structural protein expression, resulting in packaging and secretion of vector particles that could in turn be used to infect naive cells. Packaging of Sindbis virus RNA vectors expressing β-galactosidase (Dubensky et al, 1996, ibid) is accomplished by RNA transfection into PCL clones and harvesting of supernatants at 24–48 hr post-transfection. The harvested supernatants may be used to infect naive BHK-21 cells for an additional 18 hr, wherein infected cell lysates are harvested and enzymatic β-galactosidase activity determined to demonstrate packaging. Alternatively, alphavirus vectors also may be packaged by infecting the packaging cells with recombinant alphavirus vector particles or transfecting the packaging cells with an alphavirus-derived Eukaryotic Layered Vector Initiation System (U.S. Pat. No. 5,814,482), incubating the cells for a period of time sufficient for vector packaging and production (e.g., 48 hr), and harvesting the culture supernatants containing the packaged vector particles.

As should be readily apparent, substitution of the other alphavirus structural polyproteins of the present invention into these or other expression cassettes is easily accomplished using the teachings provided herein.

EXAMPLE 8

Vector Packaging with Reduced Heterologous Gene Expression

During the packaging of alphavirus vector replicons into recombinant alphavirus particles, either by RNA co-transfection with one or more defective helper RNAs or by introduction into stable alphavirus packaging cell lines, high level expression of the encoded heterologous gene (transgene) occurs. In those instances where expression of the transgene results in toxicity for the host cells, or interference with alphaviral vector replication and/or packaging, the level of recombinant alphavirus vector particles produced may be substantially decreased. To overcome this issue, the present invention provides compositions and methods for the reduction of transgene expression in specific cells that are used for alphavirus vector replicon packaging and recombinant vector particle production. The reduction of transgene expression during the packaging and particle production process provides a method to overcome the issue of toxic or interfering transgene expression, as well as to increase the overall titer of vector particles produced in those instances where transgene expression is a problem.

A. Use of Complementary (Antisense) RNA to Reduce Transgene Expression

For example, the cells used for alphavirus vector packaging may further comprise a cassette that expresses an RNA sequence complementary (e.g., antisense) to the alphavirus vector replicon (e.g., to the subgenomic junction region promoter or subgenomic mRNA). In preferred embodiments, the cells are stably transformed with said cassette that expresses intracellularly the antisense RNA. In other embodiments, the antisense RNA molecules may be supplied exogenously. A variety of promoters may be used for intracellular expression of the antisense RNA sequence, including for example RNA polymerase I, II, and III promoters or an alphavirus junction region promoter.

For example, a stably transformed cassette which produces antisense RNA complementary to the subgenomic junction region promoter region of Sindbis virus (see FIG. 4) may be constructed as follows. A plasmid known as pBGS131dlXhoI-BGHTT (WO 97/38087) is used as initial material for constructions. This plasmid contains a bovine growth hormone (BGH) transcription termination/polyadenylation signal with a SacI site immediately upstream. First, a fragment consisting of the 40 terminal nucleotides from the Sindbis virus 3'-end plus a 25 nucleotide synthetic A-tract, and flanked by NotI and SacI sites, is generated using two oligonucleotides (ID No. 20 and 21) from U.S. Pat. No. 5,814,482 as described therein. The fragment is digested with NotI and SacI, and ligated into plasmid pBGS131dlhoI-BGHTT that has also been digested with NotI and SacI, and purified from an agarose gel using GENECLEAN. The resulting construct is designated pBGSdlX-3'BGH. Next, a Sindbis virus junction region promoter plus XhoI and NotI cloning sites is inserted into the plasmid similarly to that described above in Example 7. The junction region promoter fragment is obtained as a luciferase reporter-containing fragment from plasmid pDCMVSIN-luc, by digestion with BamHI and NotI, and purification of the luciferase reporter-containing fragment from a 0.7% agarose gel using GENECLEAN. The fragment is ligated into plasmid pBGSdIX-3'BGH that also has been digested with BamHI and NotI, to generate a plasmid designated pBGSBNluc-3'BGH. Next, an RSV (polI) promoter/5'-end tRNA sequence is obtained from 987DHBB (WO 97/38087) by digestion with BglII and BamHI and purification from an agarose gel using GENECLEAN. This fragment is ligated into pBGSBNluc-3'BGH that is similarly digested with BglII and BamHI, to produce the construct pBRSV987dl-Luc3'sh. Insertion of a neomycin phosphotransferase gene (neor) into the region of nonstructural protein gene deletion as a selectable marker, is next accomplished by digestion with BspEI and BamHI, purification from an agarose gel using GENECLEAN, and ligation with a PCR-amplified $neo^r$ gene (see WO 97/38087 and Polo et al., *PNAS* 96:4598–4603, 1999) that is also digested with BspEI and BamHI, and purified from an agarose gel. The resulting expression cassette backbone is designated p987dlneo-Luc3'sh.

Finally, a cDNA corresponding to a desired antisense sequence is generated using two overlapping synthetic oligonucleotides, which will produce a fragment with XhoI and NotI sites.

AntiJRFwd
5'ATATATCTCGAGGCCATCAGAGGG-
GAAATAAAGCATCTCTACGGTGG (SEQ. ID NO. 15)
AntiJRRev
5'TATATATGCGGCCGCTGACTATTTAG-
GACCACCGTAGAGATGCTTTAT (SEQ. ID NO. 16)

For example, the oligonucleotides listed above are mixed together at equimolar concentrations in the presence of 10 MM MgC12, heated to 100° C. for 5 minutes, and cooled slowly to room temperature. The partially double-stranded molecule is then filled in using Klenow enzyme and 50 uM dNTPs. The resultant molecule is digested with XhoI and NotI, purified from a 2% NuSieve/1% agarose gel, and ligated to p987dlneo-Luc3'sh that has also been digested with XhoI and NotI, and purified from an agarose gel to remove the luciferase insert. The resulting construct is designated p987dlneo-antiJR.

In addition to this construct, variations in the junction region promoter antisense sequence may be made by altering the overall sequence length, by using complementary sequences that are 5' or 3' to those provided, or by utilizing chimeric vector replicons that have incorporated sequences from other alphavirus (e.g., subgenomic promoter or subgenomic 5'NTR sequence) or non-alphavirus sources. Furthermore, and as described below, similar antisense sequences also may be designed to hybridize directly to the alphavirus vector subgenomic mRNA.

To generate stable cell lines containing p987dlneo-antiJR or other similar cassettes, cells that will be used for replicon packaging (e.g., BHK-21, CHO, VERO) are transfected with the plasmid (e.g., using Lipofectamine, as described by the manufacturer). Approximately 24 hr post-transfection, the cells are trypsinized and re-plated in media that contains 600 ug/ml of the drug G418 (neomycin). The media is exchanged periodically with fresh G418-containing media and foci of resistant cells are allowed to grow. Cells are trypsinized and cloned by limiting dilution in 96 well tissue culture dishes, and individual cell clones are grown and expanded prior to screening for the presence of the stably transformed cassette.

Alternatively, an antisense sequence may be expressed from other variations of a cassette, such as from an RNA polymerase III (pol III) promoter. For example, an antisense sequence which binds to the region of minus strand vector RNA, inclusive of the subgenomic junction region promoter, is expressed from a cassette comprising the following ordered elements: Adenovirus 2 VA1 RNA promoter (nucleotides −70/+30), nucleotides 7562–7606 of Sindbis virus, and the RNA polymerase III consensus transcription termination sequence. These elements are cloned into a pUC-derived kanamycin-resistant plasmid DNA vector, pBGSVG (WO 97/38087), with a <PmeI-BglII-XhoI-NotI-EcoRI-PmeI> polylinker sequence and unique PacI site on the opposite side of the vector backbone.

Assembly of the desired components in the pol III-based expression cassette is performed by PCR to juxtapose the following ordered sequences:
Ad2 Stuffer (nts. 1051–10584):
5' CCATGGTCGGGACGCTCTGGCCGGTGAGGC GTGCGCAGTCGTTGACGCTCTGGA-3' (SEQ. ID NO. 17)
Ad2 VA1RNA promoter [(−70/+30)(nts. 10585–10682)]:
5' CCGTGCAAAAGGAGAGCCTGTAAGCGGGCAC TCTTCCGTGGTCTGGTGGATAAATTCGCAAGG GTATCATGGCGGACGACCGGGGTTCGAACCCCGGA-3' (SEQ. ID NO. 18)
Sindbis virus nucleotides 7562–7606
CAGAGGGGAAATAAAGCATCTCTACG- GTGGTCCTAAATAGTCAGC (SEQ. ID NO. 19)
RNA polymerase III termination sequence:
5'-GCGCTTTTTGCGC-3' (SEQ. ID NO. 20)

Juxtaposition of the sequence elements shown above to construct the pol III-based expression cassette is accomplished in two steps. The first step uses the partially complementary oligonucleotides shown below, each at 1 µM concentration in a short (10 cycle) PCR amplification:
Ad2VAsin 1F:
5'GCGGCCGCCATGGTCGGGACGCTCTGGCCGGT GAGGCGTGCGCAGTCGTTGACGCTCTGGACCG TGCAAAAGGAGAGCC-3' (SEQ. ID NO. 21)
Ad2VAsin 1 R:
5'CCCTTGCGAATTTATCCACCAGACCACGGAAG AGTGCCCGCTTACAGGCTCTCCTTTT-3' (SEQ. ID NO. 22)
Ad2VAsin 2F:
5'AATTCGCAAGGGTATCATGGCGGACGACCGG GGTTCGAACCCCGGATCTAGACCTAAAACCA AAGTACAGAGGGGAAATA-3' (SEQ. ID NO. 23)
Ad2VAsin 2R:
5'GGGGCCGCTCCGGAGCGCAAAAAGCGCGCTG ACTATTTAGGACCACCGTAGAGATGCTTTATTT CCCCTCTG-3' (SEQ. ID NO. 24)

PCR amplification of the oligonucleotides comprising the pol III-based expression cassette shown above is performed in a single reaction, using Vent polymerase and reaction conditions as suggested by the supplier, containing in addition 2 mM MgSO$_4$, 5% DMSO, and Hot Start Wax beads, with the PCR amplification protocol, as shown below.

| Temperature (° C.) | Time (Min.) | No. Cycles |
| --- | --- | --- |
| 95 | 2 | 1 |
| 95 | 0.5 | |
| 55 | 0.5 | 10 |
| 72 | 0.5 | |

The PCR product is purified using the QIAquick PCR kit, the purified product then used in a second PCR amplification, with the primer pair shown below:
Ad2 PCR 1F:
5'-ATCTTCATGCGGCCGCCATGGTCGGGAC-3' (SEQ. ID NO. 25)
Ad2 PCR 1R:
5'-ATCTTCATGCGGCCGCTCCGGAGCGCAA-3' (SEQ. ID NO. 26)

The second PCR amplification of the pol III-based cassette is performed with the Vent polymerase and similar reaction conditions, with the PCR amplification protocol, as shown below.

| Temperature (° C.) | Time (Min.) | No. Cycles |
| --- | --- | --- |
| 95 | 2 | 1 |
| 95 | 0.5 | |
| 55 | 0.5 | 20 |
| 72 | 0.5 | |
| 72 | | 1 |

The products of this second PCR reaction are purified with the QIAquick kit, digested with NotI, re-purified and then inserted into the vector pBGSVG that has also been digested with NotI and treated with alkaline phosphatase. This plasmid is designated pAntiSINjr.

Insertion of a hygromycin drug selectable marker into pAntiSINjr is accomplished using the unique PacI site in the vector backbone. A hygromycin marker cassette, under the control of an HSV TK promoter, is isolated from plasmid pBGSVhygro-G (WO 97/38087) by digestion with PacI and purification from an agarose gel using GENECLEAN. The isolated fragment then is ligated into pAntiSINjr that has also been digested with PacI, resulting in a plasmid construct designated pAntiSINjrHyg.

Plasmid pAntiSINjrHyg is transfected into a desired cell type (e.g., BHK-21, CHO, VERO) and approximately 24 hr post-transfection, the cells are trypsinized and re-plated in media containing 500 ug/ml of hygromycin (Boehringer Mannheim). The media is exchanged periodically with fresh drug-containing media and foci of resistant cells are allowed to grow. Cells are trypsinized, cloned by limiting dilution in 96 well plates, and the resulting cell lines screened for the stably transformed cassette.

Initially, demonstration of reduced transgene expression in the antisense cell lines from Sindbis or other similar alphavirus replicon vectors is accomplished by linearization and in vitro transcription of a reporter vector, as described previously. The in vitro transcribed vector RNA is then transfected or electroporated into the modified cells, as well as control parental cells, followed by harvest of cell lysates at 12 and 24 hr post-transfection. Reporter gene expression is quantitated as previously described (Dubensky et al, 1996, ibid; Polo et al, 1999, ibid; U.S. Pat. No. 5,789,245; WO 97/38087), and compared between the cell lines. Decreased expression in the modified cells, as compared to the parental cells, is indicative of specific transgene suppression. These systems may be similarly used in a variety of cell lines for the packaging of alphavirus vector particles, and established methods for packaging are provided elsewhere (U.S. Pat. No. 5,789,245, Dubensky et al, 1996, ibid; Polo et al., 1999, ibid).

In another embodiment of the present invention, chimeric alphavirus replicons, as well as chimeric alphavirus glycoprotein defective helper cassettes are disclosed. In such chimeras, the wild-type subgenomic promoter or subgenomic 5'-nontranslated (NTR) region of one alphavirus is substituted with the corresponding region from another alphavirus. Such chimeras provide a number of advantages for use in the present invention. For example, by using different subgenomic promoter or 5'-NTR sequences, transgene expression from one vector or defective helper RNA can be preferentially targeted with antisense molecules, while not affecting other vector or defective helper RNAs that contain the wild-type sequence. Furthermore, the incorporation of a specific 5'-NTR from an alphavirus whose subgenomic translational enhancer element does not extend into the capsid gene coding sequence (e.g., from Venezuelan equine encephalitis virus, VEE), may overcome potential expression issues for vector and defective helper RNAs derived from alphaviruses that do require such a capsid-inclusive element (e.g., Sindbis and Semliki Forest virus).

Specifically, in one embodiment, a Sindbis virus-derived vector replicon and glycoprotein defective helper (U.S. Pat. No. 5,789,245, Polo et al., ibid) was modified to contain the subgenomic 5'NTR sequence from VEE. In one strategy, these constructs are generated using a cDNA fragment comprising both the Sindbis virus subgenomic promoter and the VEE subgenomic 5'-NTR that is synthesized by PCR using overlapping oligonucleotides. These oligonucleotides further contain BamHI and XhoI restriction sites for convenient substitution into the final constructs.

VEE5'NTR1:
5'ATATAGGATCCCCTGAAAAGGCTGTT-TAAGTTGGGTAAACCGCTCCCAGCCGAC-GACGAGCAAGACGAAGACAGAAGACGC (SEQ ID NO:35)

VEE5'NTR2:
5' CCACTGCTAAAGTGCCTGTTATAC-CTACTCTAAACCACGC-CTTTGTTTCATCTAGCAGAGCGCGTCT-TCTGTCTTCGTCTT (SEQ ID NO:36)

VEE5'NTR3:
5'AACAGGCACTTTAGCAGTGGCCGTGAC-GACCCGGTATGAGGTAGACAATATTA-CACCTGTCCTACTGGCAT-TGAGAACTTTTGCCCAGAGCAAAAGAGCATT CCAAGC (SEQ ID NO:37)

VEE5'NTR4:
5'ATATACTCGAGCTTGGCGGACTAGAC-TATGTCGTAGTCTATTTAGGACCACCG-TAGAGATGCTTTATTTCCCCTCTGATG-GCTTGGAATGCTCTTTTGCT (SEQ ID NO:38)

PCR amplification of the oligonucleotides shown above is performed in a single reaction, using Vent polymerase and reaction conditions as suggested by the supplier, containing in addition 2 mM $MgSO_4$, 5% DMSO, and Hot Start Wax beads, with the PCR amplification protocol, as shown below.

| Temperature (° C.) | Time (Min.) | No. Cycles |
|---|---|---|
| 95 | 2 | 1 |
| 95 | 0.5 | |
| 55 | 0.5 | 10 |
| 72 | 0.5 | |

The PCR product is purified using the QIAquick PCR kit, and then the purified product is used in a second PCR amplification, with the primer pair shown below:

VEE5'NTR5:
5'ATATAGGATCCCCTGA (SEQ ID NO:39)

VEE5'NTR6:
5'ATATACTCGAGCTTGG (SEQ ID NO:40)

Following an additional purification step, the synthesized PCR fragment is digested with BamHI and XhoI, and ligated into a Sindbis replicon vector and glycoprotein defective helper that were similarly digested with BamHI and XhoI. An additional final cloning step is required for the replicon construct, due to the unwanted deletion of a BamHI-BamHI nonstructural gene fragment. This fragment is obtained from another preparation of replicon DNA by BamHI digestion and gel purification, followed by ligation into the new VEE 5'NTR containing replicon that also has been digested with BamHI and treated with alkaline phosphatase. Similar constructs containing the VEE sequence may readily be generated for other alphavirus replicon vectors and defective helpers (e.g., Semliki Forest virus, Ross River virus) by one of skill in the art using the teachings provided herein.

B. Use of Aptamer-Ligand Combinations to Reduce Transgene Expression

Figure 6:
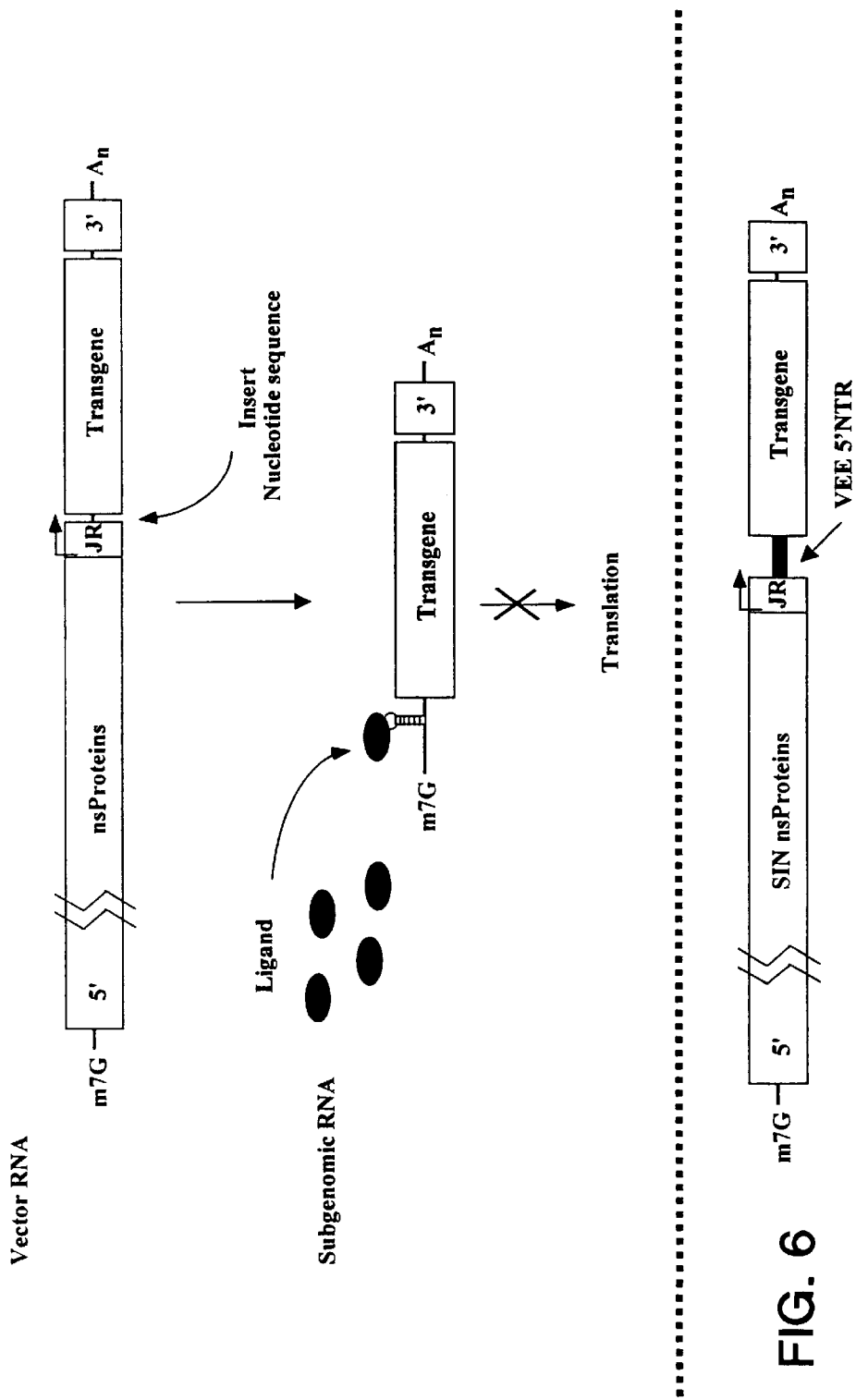
FIG. 6 is a schematic illustration of a method of reducing heterologous transgene expression from alphavirus vectors using a specific inserted nucleotide sequence and supplied corresponding ligand.

Alternatively, an aptamer RNA and ligand pair combination as described herein may be using to reduce transgene expression. In such an approach, the replicon vector to be packaged is modified by insertion of the aptamer sequence and then the appropriate ligand is provided to the cells during vector packaging by either transient co-transfection or packaging cell line methods (see FIG. 6). For example, H10 and H19 aptamers (Werstuck and Green, Science 282:296–298), are generated as a tandem pair (single copy each) by PCR using overlapping oligonucleotides which produce flanking and internal restriction sites for manipulation. The aptamer sequences are shown below:

H10 Aptamer sequence
GGTGATCAGATTCTGATCCAATGTTAT-GCTTCTCTGCCTGGGAACAGCTGCCT-GAAGCTTTGGATCCGTCGC (SEQ. ID NO. 27)

H19 Aptamer sequence
GGTGATCAGATTCTGATCCAACAGGT-TATGTAGTCTCCTACCTCTGCGCCT-GAAGCTTGGATCCGTCGC (SEQ. ID NO. 28)

To demonstrate the ability of these aptamers to reduce transgene expression from alphavirus vectors in the presence of their ligands, Hoechst dye H33258 or H33342, a reporter vector is first constructed with the aptamer sequence inserted at a site which corresponds to the 5'-nontranslated region of the subgenomic RNA, immediately upstream of the AUG initiator codon for the reporter gene. Vectors containing other transgenes may be constructed in a similar manner, and alternatively, may also contain aptamer insertion at other sites.

In order to construct an alphavirus-derived vector containing the above aptamer insert, a previously described Sindbis vector is modified to position a unique XhoI site just downstream and adjacent to the subgenomic transcription start site. This is accomplished by PCR amplification using the following two oligonucleotides:

SIN5122F:
5'ATATATGGCCGAAGAGGCCCCCGAAGTTGTAG (SEQ. ID NO. 29)

SIN7600R:
5'ATATATCTCGAGTATTTAGGACCACCG-TAGAGATGC (SEQ. ID NO. 30)

The forward primer (SIN5122F) contains a unique SfiI site within the Sindbis virus nsP3 sequence, while the reverse primer (SIN7600R) contains the junction region promoter and a AhoI site. PCR is performed using VENT polymerase and plasmid pRSIN-β-gal (Dubensky et al., 1996, ibid) as template. The approximately 2.5 kbp fragment is purified using the QIAquick kit, digested with SfiI and XhoI, and ligated to plasmid pRSIN-β-gal that has also been digested with SfiI and XhoI to remove the corresponding fragment, and purified from an agarose gel using GENECLEAN. The new Sindbis virus vector construct is designated pRSINjr-βgal.

Generation of the aptamer sequence for insertion into this vector is accomplished using a series of overlapping oligonucleotides listed below to produce a fragment comprising the following ordered elements: 5'-SalI site/AatII site/H10 Aptamer/PacI site/H19 Aptamer/XhoI site/NotI site-3'.

AptH10Fwd1:
5'ATATATGTCGACGTCGGTGATCAGAT-TCTGATCCAATGTTATGCTTCTCTGC-CTGGGAACAGC (SEQ. ID NO. 31)

AptH10Rev1:
5'TCTGATCACCTTAATTAAGCGACGGATC-CAAAGCTTCAGGCAGCTGTTCCCAGGCA-GACAAGCATA (SEQ. ID NO. 32)

AptH19Fwd1:
5'GCTTAATTAAGGTGATCAGATTCTGATC-CAACAGGTTATGTAGTCTCCTACCTCTGCG (SEQ. ID NO. 33)

AptH19Rev1:
5=ATATATGCGGCCGCATATCTCGAGGC-GACGGATCCAAGCTTCAGGCGCAGAGG-TAGGAGACTACATAAC (SEQ. ID NO. 34)

The partially complementary oligonucleotides listed above are first used at 1 μM concentration in a short (10 cycle) single PCR amplification reaction, with VENT polymerase as suggested by the supplier, containing in addition 2 mM MgSO$_4$, 5% DMSO, and Hot Start Wax beads (Perkin-Elmer), with a PCR amplification protocol, as shown below.

| Temperature (° C.) | Time (Min.) | No. Cycles |
| --- | --- | --- |
| 95 | 2 | 1 |
| 95 | 0.5 | |
| 55 | 0.5 | 10 |
| 72 | 0.5 | |

The PCR product is purified with the QIAquick kit and then used in a second PCR amplification, with the primer pair AptHIOFwd1 and AptH19Rev1 and additional cycles, under similar conditions. The products of this second PCR reaction again are purified with QIAquick, digested with SalI and NotI, and then inserted into plasmid pRSINjr-βgal that has been digested with XhoI and NotI, and gel-purified to remove the βgal insert. This vector plasmid is designated pRSINapt-empty. The β-gal insert is then re-inserted into the vector by digestion of pRSINjr-βgal with XhoI and NotI, purification of the fragment from an agarose gel, and ligation into similarly digested and gel-purified plasmid pRSINapt-empty. The resulting reporter vector construct is pRSINapt-βgal.

Demonstration of the reduction in transgene translation as compared to the unmodified parental vector is accomplished by linearization and in vitro transcription of both vectors as described previously. The in vitro transcribed vector RNAs are then transfected or electroporated into cells that are growing in Hoechst dyes H33258 or H33342, ranging in concentration from 5 to 50 mM. At 12 and 24 hr post-transfection, cell lysates are obtained and reporter gene expression is quantitated as previously described (Dubensky et al, 1996 ibid, U.S. Pat. No. 5,789,245, and WO 97/38087).

Of particular interest, insertion of artificial stem-loop structures (e.g., aptamers) into the 5' non-translated region of alphavirus subgenomic RNA as disclosed herein, also may provide a mechanism to enhance translation (e.g., in the absence of ligand), by substituting for the native alphavirus stem-loop translational enhancer structure in this region.

In another embodiment of this technology, the bacteriophage R17 coat protein and corresponding specific RNA ligand may be used to reduce transgene expression. The RNA binding site for bacteriophage R17 coat protein (Krug et al. 1982, *Biochemistry* 21:4713–4720) can be introduced into the vector at a site that corresponds to the 5' end of the subgenomic mRNA. The minimal R17 binding site comprises a sequence AAACAUGAGGAUUACCCAUGU (SEQ ID NO:41) and forms a stem loop structure absolutely required for binding. Analysis of a population of high affinity RNA ligands to the coat protein revealed the components of a hairpin that promote favorable interactions with the coat protein (Schneider et al. 1992 *J. Mol. Biol.* 228:862–869).

To demonstrate the ability of this R17 binding site to reduce transgene expression from alphavirus vectors in the presence of the R17 coat protein, variants of the binding site were introduced into a Sindbis vector at a site corresponding to the 5'-nontranslated (NTR) region of subgenomic mRNA, immediately upstream of the AUG initiator codon for a reporter transgene. Additional vectors containing other transgenes may be readily constructed in a similar manner by one of skill in the art using the teachings provided herein.

Two binding sites were designed to include components essential for both high affinity binding to the coat protein and high efficiency of replication and subgenomic transcription of the Sindbis virus derived vectors (FIG. 7). In both binding sites, specific elements were introduced comprising: 1) in the loop, a C replaced $U_{13}$ to maximize functionality of this structure in Eukaryotic cells, and 2) the two pairs $G_9$-$C_{16}$, $G_{10}$-$C_{15}$ were inverted. Furthermore, one binding site also included 1) the substitution of the pair $U_{16}$-$A_{18}$ into G-C in the stem loop to eliminate the AUG codon, and 2) the substitution of $A_1A_2$ with first 5 nucleotides (AUAGU) of Sindbis 5'-nontranslated region which are essential for subgenomic transcription. This binding site was named 5TOP. The other binding site was designed to include the first 5 nucleotides of Sindbis 5'-nontranslated region in the stem, resulting in the substitution of the pairs $A_3$-$U_{21}$, $C_4$-$G_{20}$, $A_5$-$U_{19}$, and $G_7C_{,7}$ with the pairs U-A, A-U, G-C, and C-G respectively. This binding site was named TOP.

Introduction of the 5TOP binding site was accomplished by PCR amplification of two overlapping fragments also generated by PCR amplification, as follows:

5TOPF:
5'-CAGCACCATCAGGGCTGGCAGCATAGTACAT TTCATCTGAC (SEQ ID NO:42)
SCG8120R:
5'-CGTTGTGGCTGTTGTAGTTGTAC (SEQ ID NO:43)

In the forward primer (5TOPF), bases 1–19 are the R17 coat protein-binding site, while bases 20–42 are complementary to nt. 7603–7625 of the Sindbis replicon vector expressing a GFP reporter (SINCR-GFP). The reverse primer is complementary to nt. 8105–8083 of the same vector.

The second fragment was amplified using the following two oligonucleotides:
SCR728F:
5'-TGCGGCGGATTTATCTTGCAAG (SEQ ID NO:44)
5TOPR:
5'-CAGCCCTGATGGTGCTGGACTATTTAGGACCA CCGTAGAG (SEQ ID NO:45)

The forward primer is complementary to the 7281–7302 nt. of the Sindbis GFP reporter vector, while the reverse primer contains the R 17 coat protein binding site in nts. 1–19, and nts. 20–41 are complementary to 7581–7602 of the Sindbis vector. The oligonucleotides were used at 2 µM concentration with 0.1 µg of plasmid template in a single, 10-cycle PCR reaction with Pfu Polymerase, as suggested by the supplier. The amplification protocol is shown below.

| Temperature (° C.) | Time (Min.) | No. Cycles |
| --- | --- | --- |
| 94 | 2 | 1 |
| 94 | 0.5 | |
| 60 | 0.5 | 10 |
| 72 | 2 | |

The two amplified fragments were purified from an agarose gel using a QIAquick gel extraction kit, and an aliquot of each fragment was used as template for a second PCR amplification. The two fragments were mixed with Vent Polymerase as suggested by supplier, and one PCR amplification cycle was performed:

| Temperature (° C.) | Time (Min.) | No. Cycles |
| --- | --- | --- |
| 94 | 2 | 1 |
| 94 | 0.5 | |
| 42 | 1 | 1 |
| 72 | 3 | |

The following primers, overlapping respectively with the BamHI$_{7335}$ and XhoI sites of the Sindbis replicon, then were added at a 2 µM concentration:
SCR7320F:
5' ATATATGCGTGCCGCGTGGCGGATCCCC (SEQ ID NO:46)
SCRG7672R:
5' ATATATCATGGTGGCTCGAGGGTGGTGTT (SEQ ID NO:47)

PCR amplification was performed as follows:

| Temperature (° C.) | Time (Min.) | No. Cycles |
| --- | --- | --- |
| 94 | 2 | 1 |
| 94 | 0.5 | |
| 60 | 0.5 | 30 |
| 72 | 2 | |

The PCR product (300bp) was purified using the QIAquick kit, digested with BamHI and XhoI, gel purified from agarose gel as described above, and ligated into plasmid SINCR-GFP that had also been digested with BamHI and XhoI and purified from an agarose gel. Clones containing the inserts were verified by sequencing and, finally, the BamHI$_{4634}$-BamHI$_{7355}$ was reinserted into this construct. The new Sindbis virus vector construct was designated SINCR-5TOP-GFP.

The second Sindbis derived vector was constructed in a similar manner, with the only differences being the forward oligonucleotide primer for the PCR amplification of the first fragment, as follows:
TOPF:
5' CACCATCAGGGACTACAGCATAGTA-CATTTCATCTGAC (SEQ ID NO:48)
and, the reverse primer for the PCR amplification of the second fragment, as follows:
TOPR:
5' TAGTCCCTGATGGTGACTATTTAGGAC-CACCGTAGAG (SEQ ID NO:49)

Following insertion of the overlapping PCR fragment into the SINCR-GFP vector, this new Sindbis replicon construct was designated SINCR-TOP-GFP.

Next, the ability of these new vectors to express the reporter gene GFP and to be packaged into vector particles was demonstrated. Plasmid DNA from these two new constructs and from the parental construct were linearized and used for in vitro transcription as described previously. Each transcript was co-transfected into BHK cells with together with helper RNAs expressing capsid and glycoproteins (Polo et al., 1999, ibid). Transfected cells were incubated for 24 hr, at which time the culture supernatants were collected and the cells harvested. The harvested cells were analyzed by flow cytometry. The supernatants were clarified by centrifugation, serially diluted and used to infect in duplicate, naïve BHK-21 cells for approximately 14 hr. The infected cells were counted based on GFP fluorescence to determine vector particle titer in the original supernatants. Both constructs efficiently expressed GFP reporter and were packaged into recombinant alphavirus vector particles.

Figure 8:
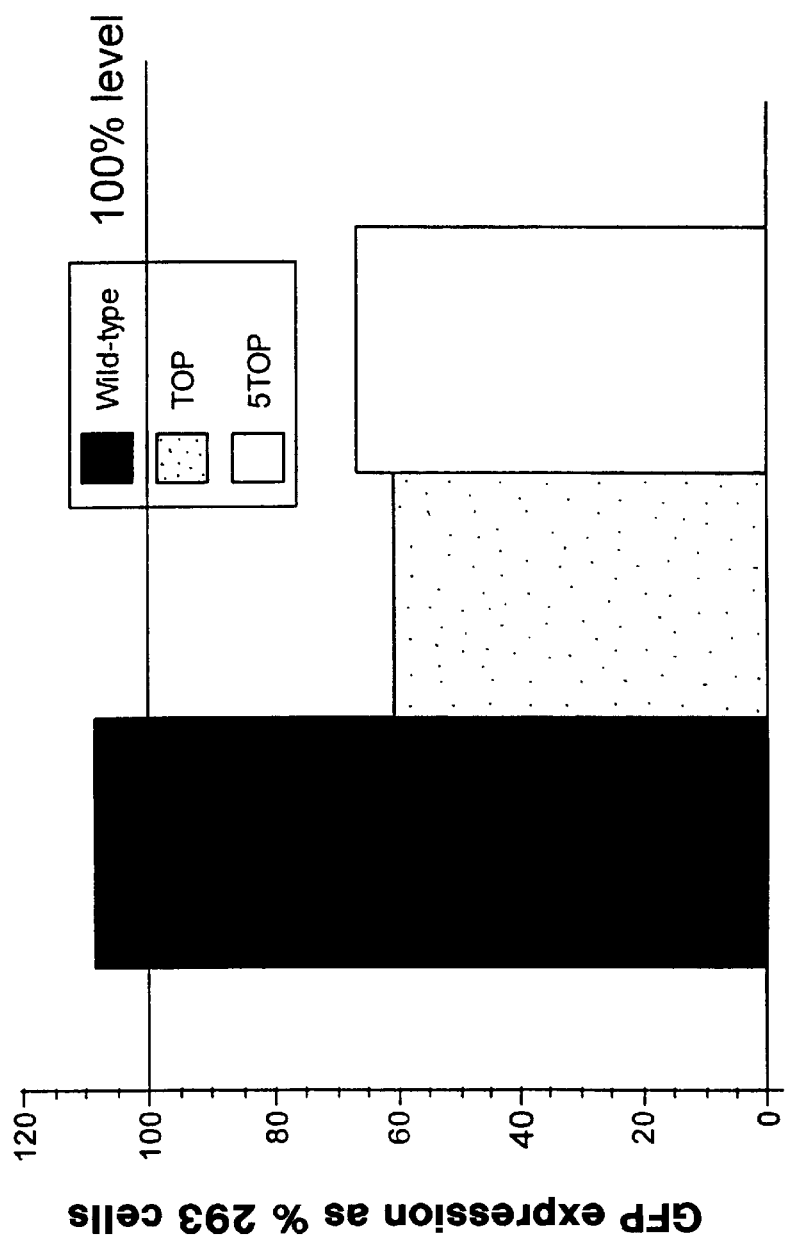
FIG. 8 is a graph demonstrating reduced expression of a heterologous transgene by an RNA binding protein specific for the sequence modifications in FIG. 7.

To demonstrate that transgene expression can be down-regulated in the presence of R17 coat protein, vector particles derived from both modified constructs, as well as the parental construct, were used to infect at an MOI=3, 293 cells and 293 derivative cells that express the R17 coat protein. Following incubation for 24 hrs, GFP expression was analyzed by flow cytometry. As shown in FIG. 8, expression of the GFP transgene was reduced significantly in R17-expressing 293 cells (as compared to wild-type 293 cells) for each of the modified vector replicons, but not for the wild-type SINCR replicon. The R17 coat protein similarly may be expressed in a variety of cell lines for use in the packaging of alphavirus vector particles, and established methods for packaging are provided elsewhere (U.S. Pat. No. 5,789,245, Dubensky et al, 1996, ibid; Polo et al., 1999, ibid). These data demonstrate the ability to specifically down-regulate transgene expression from alphavirus vectors, using methods of the present invention.

To utilize this approach for packaging of an alphavirus replicon in the absence of high level expression of the vector encoded heterologous transgene, stable alphavirus vector packaging cell lines capable of expressing the R17 coat protein were generated. Using the parental alphavirus packaging cell line, PCL 15.25, which expresses the Sindbis virus capsid and envelope glycoproteins from stably integrated structural protein cassettes, plasmids pBS-CP, which expresses the R17 coat protein from a CMV promoter, and pPur (Invitrogen), which encodes the puromycin resistance gene, were introduced. The two plasmids were co-transfected into the cells at the ratios of 10 or 20 to 1 respectively using lipofectamine (GIBCO). Approximately 24 hrs post-transfection, the cells were treated with trypsin and plated into medium containing 4.5 µg/ml puromycin. The medium was replaced with fresh puromycin-containing media every three days until puromycin resistant colonies were visible. Following dilution cloning and expansion, the clones were functionally screened by infection with SINCR-5TOP-GFP particles at an MOI=2, followed by flow cytometry approximately 24 post-infection to measure the levels of GFP expression. The clones that showed the lowest amounts of GFP expression were presumably the ones that expressed the R17 coat protein in sufficient amounts to repress the heterologous expression from the alphaviral replicons. To confirm the screening, these clones and parental PCL 15.25 cells were infected with SINCR-5TOP-GFP, SINCR-TOP-GFP, or SINCR-GFP vector particles at an MOI=2. Approximately 24 hrs post-infection, the cells were harvested and analyzed by flow cytometry. One positive clone was designated CPPCL. FIG. 9 shows CPPCL and PCL cell lines 24 hrs after infection with the SINCR-GFP, SINCR-TOP-GFP, or SINCR-5TOP-GFP particles and FIG. 10 shows a summary of the results from the flow cytometry analysis. These results clearly demonstrate that CPPCL can efficiently repress heterologous transgene expression from the modified SINCR-5TOP-GFP and SINCR-TOP-GFP alphavirus vectors during their replication.

To demonstrate that this system did not preclude the generation of high titer preparations of recombinant vector particles, the packaging efficiency of the CPPCL cell line was measured and compared to the parental PCL cell line. Both cell lines were infected at an MOI=0.5 with SINCR-5TOP-GFP, SINCR-TOP-GFP, or SINCR-GFP particles. Supernatants were harvested and replaced with fresh medium approximately every 12 hrs. over 2 days. Serial dilutions of the supernatants were used to infect naïve BHK21 and the culture supernatants were analyzed by flow cytometry to calculate the vector particle titers produced. No significant differences were observed in the titers of particles obtained from the two cell lines with all any of the vectors. These data demonstrate the utility of this packaging cell line to generate high titer vector particles with concomitant down-regulation of transgene expression.

While the present invention has been described above both generally and in terms of preferred embodiments, it is understood that variations and modifications will occur to those skilled in the art in light of the description, supra. Therefore, it is intended that the appended claims cover all such variations coming within the scope of the invention as claimed.

We claim:

1. An RNA vector, comprising a 5' sequence which initiates transcription of alphavirus RNA, an alphavirus subgenomic region promoter, a sequence from a subgenomic 5' end nontranslated region from Venezuelan equine encephalitis (VEE), a sequence encoding one or more alphavirus structural proteins and a 3' alphavirus RNA polymerase recognition sequence, wherein said vector does not encode all biologically active alphavirus nonstructural proteins, and wherein said 5' sequence which initiates transcription and said 3' alphavirus RNA polymerase recognition sequence are not from VEE.

2. The RNA vector according to claim 1 wherein said alphavirus structural proteins are glycoproteins E2 and E1.

3. The RNA vector according to claim 1 wherein said 5' sequence which initiates transcription and 3' alphavirus RNA polymerase recognition sequence are Sindbis virus or Semliki Forest virus sequences.

4. The RNA vector according to claim 1 wherein said alphavirus structural proteins are Sindbis virus or Semliki Forest virus structural proteins.

5. The RNA vector according to claim 1 further comprising a polyadenylation tract.

6. An alphavirus vector construct, comprising a 5' promoter operably linked to a nucleic acid molecule, wherein said nucleic acid molecule is complementary DNA to the RNA vector according to claim 1.

7. The alphavirus vector construct according to claim 6 wherein said promoter is a eukaryotic promoter.

8. The alphavirus vector construct according to claim 6 wherein said promoter is a bacteriophage promoter.

9. An alphavirus packaging cell comprising one or more alphavirus structural protein expression cassettes and an expression cassette comprising a promoter that is operably linked to a nucleic acid molecule, which when transcribed produces an RNA sequence complementary to an alphavirus junction region promoter, or, alphavirus subgenomic RNA, wherein said nucleic acid molecule is less that 500 nucleotides in length.

10. An alphavirus packaging cell comprising one or more alphavirus structural protein cassettes and an expression cassette comprising a promoter that is operably linked to a nucleic acid molecule which encodes R17 coat protein.

* * * * *

SEQUENCE LISTING

<160> NUMBER OF SEQ ID NOS: 51

<210> SEQ ID NO 1
<211> LENGTH: 24
<212> TYPE: DNA
<213> ORGANISM: Sindbis virus

<400> SEQUENCE: 1
atctctacgg tggtcctaaa tagt                                          24

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer for
     PCR amplification

<400> SEQUENCE: 2
ctcgagacca tgaatagagg attctttaac                                    30

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Primer for
     PCR amplification

<400> SEQUENCE: 3

-continued gcggccgctc aagcattggc cgacctaacg cagcac                36

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 4
ggatccgtcg tcaacgacgc ttcttttgc                        29

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 5
ggatccaggt cggccaatgc tgaaacgttc accgagacca tgagttac   48

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 6
gcggccgctc atcttcgtgt gctagtcagc atc                   33

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 7
ctcggtgaac gtttctgcgg accactcttc tgtcccttc             39

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 8
gaagagtggt ccgcagaaac gttcaccgag accatgag              38

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 9
atatatctcg agcaccatga atagaggatt ctttaac               37

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 10
gtggtcgcat gttcgcttct tttgcttctg ccagacg                              37

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 11
gaagcaaaag aagcgaacat gcgaccactg ttccaaatg                            39

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 12
tatatagcgg ccgctcatct tcgtgtgcta gtcagcatc                            39

<210> SEQ ID NO 13
<211> LENGTH: 75
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 13
tgctccacac agcagcagca cacagcagag ccctctcttc attgcatctg cggaccactc      60
ttctgtccct tccgg                                                      75

<210> SEQ ID NO 14
<211> LENGTH: 75
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 14
tgtgtgctgc tgctgtgtgg agcagtcttc gtttcgccca gcgctagcta cgaacatgcg      60
accactgttc caaat                                                      75

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide for PCR amplification

```
<400> SEQUENCE: 15
atatatctcg aggccatcag agggggaaata aagcatctct acgtgg          47

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide for PCR amplification

<400> SEQUENCE: 16
tatatatgcg gccgctgact atttaggacc accgtagaga tgctttat         48

<210> SEQ ID NO 17
<211> LENGTH: 54
<212> TYPE: DNA
<213> ORGANISM: adeno-associated virus 2

<400> SEQUENCE: 17
ccatggtcgg gacgctctgg ccggtgaggc gtgcgcagtc gttgacgctc tgga   54

<210> SEQ ID NO 18
<211> LENGTH: 98
<212> TYPE: DNA
<213> ORGANISM: adeno-associated virus 2

<400> SEQUENCE: 18
ccgtgcaaaa ggagagcctg taagcgggca ctcttccgtg gtctggtgga taaattcgca   60
agggtatcat ggcggacgac cggggttcga accccgga                          98

<210> SEQ ID NO 19
<211> LENGTH: 45
<212> TYPE: DNA
<213> ORGANISM: Sindbis virus

<400> SEQUENCE: 19
cagaggggaa ataaagcatc tctacggtgg tcctaaatag tcagc            45

<210> SEQ ID NO 20
<211> LENGTH: 13
<212> TYPE: DNA
<213> ORGANISM: Unknown
<220> FEATURE:
<223> OTHER INFORMATION: Description of Unknown Organism:  RNA
      ploymerase III consensus transcription termination sequence

<400> SEQUENCE: 20 gcgcttttg cgc                                                13

<210> SEQ ID NO 21
<211> LENGTH: 79
<212> TYPE: DNA
<213> ORGANISM: Artificial Sequence
<220> FEATURE:
<223> OTHER INFORMATION: Description of Artificial Sequence:
      Oligonucleotide for PCR amplification

<400> SEQUENCE: 21
gcggccgcca tggtcgggac gctctggccg gtgaggcgtg cgcagtcgtt gacgctctgg   60
accgtgcaaa aggagagcc                                               79

<210> SEQ ID NO 22
```

<211> LENGTH: 58
<212> TYPE: DNA
<213> ORGANISM: Artificial Sequence
<220> FEATURE:
<223> OTHER INFORMATION: Description of Artificial Sequence:
      Oligonucleotide for PCR amplification

<400> SEQUENCE: 22
cccttgcgaa tttatccacc agaccacgga agagtgcccg cttacaggct ctccttt    58

<210> SEQ ID NO 23
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide for PCR amplification

<400> SEQUENCE: 23
aattcgcaag ggtatcatgg cggacgaccg gggttcgaac cccggatcta gacctaaaac    60
caaagtacag agggaaata                                                 80

<210> SEQ ID NO 24
<211> LENGTH: 72
<212> TYPE: DNA
<213> ORGANISM: Artificial Sequence
<220> FEATURE:
<223> OTHER INFORMATION: Description of Artificial Sequence:
      Oligonucleotide for PCR amplification

<400> SEQUENCE: 24
gcggccgctc cggagcgcaa aaagcgcgct gactatttag gaccaccgta gagatgcttt    60
atttcccctc tg                                                        72

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence:  Primer for
      PCR amplification

<400> SEQUENCE: 25
atcttcatgc ggccgccatg gtcgggac                                       28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:  Primer for
      PCR amplification

<400> SEQUENCE: 26
atcttcatgc ggccgctccg gagcgcaa                                       28

<210> SEQ ID NO 27
<211> LENGTH: 72
<212> TYPE: DNA
<213> ORGANISM: Unknown
<220> FEATURE:
<223> OTHER INFORMATION: Description of Unknown Organism:  See Werstuck
      & Green, Science 282: 296-298, 1998.  Isolated
      aptamer that binds specifically to Hoechst dye
      H33258.

<400> SEQUENCE: 27

```
ggtgatcaga ttctgatcca atgttatgct tctctgcctg ggaacagctg cctgaagctt    60
tggatccgtc gc                                                        72
```

<210> SEQ ID NO 28
<211> LENGTH: 69
<212> TYPE: DNA
<213> ORGANISM: Unknown
<220> FEATURE:
<223> OTHER INFORMATION: Description of Unknown Organism: See Werstuck
      & Green, Science 282: 296-298, 1998. Isolated
      aptamer that binds specifically to Hoechst dye
      H33258.

<400> SEQUENCE: 28

```
ggtgatcaga ttctgatcca acaggttatg tagtctccta cctctgcgcc tgaagcttgg    60
atccgtcgc                                                            69
```

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide for PCR amplification

<400> SEQUENCE: 29

```
atatatggcc gaagaggccc ccgaagttgt ag                                  32
```

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide for PCR amplification

<400> SEQUENCE: 30

```
atatatctcg agtatttagg accaccgtag agatgc                              36
```

<210> SEQ ID NO 31
<211> LENGTH: 63
<212> TYPE: DNA
<213> ORGANISM: Artificial Sequence
<220> FEATURE:
<223> OTHER INFORMATION: Description of Artificial Sequence:
      Oligonucleotide for PCR amplification

<400> SEQUENCE: 31

```
atatatgtcg acgtcggtga tcagattctg atccaatgtt atgcttctct gcctgggaac    60
agc                                                                  63
```

<210> SEQ ID NO 32
<211> LENGTH: 66
<212> TYPE: DNA
<213> ORGANISM: Artificial Sequence
<220> FEATURE:
<223> OTHER INFORMATION: Description of Artificial Sequence:
      Oligonucleotide for PCR amplification

<400> SEQUENCE: 32

```
tctgatcacc ttaattaagc gacggatcca aagcttcagg cagctgttcc caggcagaga    60
agcata                                                               66
```

```
<210> SEQ ID NO 33
<211> LENGTH: 58
<212> TYPE: DNA
<213> ORGANISM: Artificial Sequence
<220> FEATURE:
<223> OTHER INFORMATION: Description of Artificial Sequence:
      Oligonucleotide for PCR amplification

<400> SEQUENCE: 33
gcttaattaa ggtgatcaga ttctgatcca acaggttatg tagtctccta cctctgcg        58

<210> SEQ ID NO 34
<211> LENGTH: 69
<212> TYPE: DNA
<213> ORGANISM: Artificial Sequence
<220> FEATURE:
<223> OTHER INFORMATION: Description of Artificial Sequence:
      Oligonucleotide for PCR amplification

<400> SEQUENCE: 34
atatatgcgg ccgcatatct cgaggcgacg gatccaagct tcaggcgcag aggtaggaga       60
ctacataac                                                              69

<210> SEQ ID NO 35
<211> LENGTH: 81
<212> TYPE: DNA
<213> ORGANISM: Artificial Sequence
<220> FEATURE:
<223> OTHER INFORMATION: PCR amplified oligonucleotide

<400> SEQUENCE: 35
atataggatc ccctgaaaag gctgtttaag ttgggtaaac cgctcccagc cgacgacgag       60
caagacgaag acagaagacg c                                                81

<210> SEQ ID NO 36
<211> LENGTH: 81
<212> TYPE: DNA
<213> ORGANISM: Artificial Sequence
<220> FEATURE:
<223> OTHER INFORMATION: PCR amplified oligonucleotide

<400> SEQUENCE: 36
ccactgctaa agtgcctgtt atacctactc taaaccacgc ctttgtttca tctagcagag       60
cgcgtcttct gtcttcgtct t                                                81

<210> SEQ ID NO 37
<211> LENGTH: 108
<212> TYPE: DNA
<213> ORGANISM: Artificial Sequence
<220> FEATURE:
<223> OTHER INFORMATION: PCR amplified oligonucleotide

<400> SEQUENCE: 37
aacaggcact ttagcagtgg ccgtgacgac ccggtatgag gtagacaata ttacacctgt       60
cctactggca ttgagaactt ttgcccagag caaaagagca ttccaagc                   108

<210> SEQ ID NO 38
<211> LENGTH: 100
<212> TYPE: DNA
<213> ORGANISM: Artificial Sequence
<220> FEATURE:
<223> OTHER INFORMATION: PCR amplified oligonucleotide

<400> SEQUENCE: 38
```

```
atatactcga gcttggcgga ctagactatg tcgtagtcta tttaggacca ccgtagagat      60
gctttatttc ccctctgatg gcttggaatg ctcttttgct                            100
```

<210> SEQ ID NO 39
<211> LENGTH: 16
<212> TYPE: DNA
<213> ORGANISM: Artificial Sequence
<220> FEATURE:
<223> OTHER INFORMATION: Primer for PCR amplification

<400> SEQUENCE: 39

```
ataggatc ccctga                                                        16
```

<210> SEQ ID NO 40
<211> LENGTH: 16
<212> TYPE: DNA
<213> ORGANISM: Artificial Sequence
<220> FEATURE:
<223> OTHER INFORMATION: Primer for PCR amplification

<400> SEQUENCE: 40

```
atatactcga gcttgg                                                      16
```

<210> SEQ ID NO 41
<211> LENGTH: 21
<212> TYPE: RNA
<213> ORGANISM: Artificial Sequence
<220> FEATURE:
<223> OTHER INFORMATION: Synthesized oligoribonucleotide identical with
      the bacteriophage R17 replicase initiator region

<400> SEQUENCE: 41

```
aaacaugagg auuacccaug u                                                21
```

<210> SEQ ID NO 42
<211> LENGTH: 41
<212> TYPE: DNA
<213> ORGANISM: Artificial Sequence
<220> FEATURE:
<223> OTHER INFORMATION: Primer for PCR amplification

<400> SEQUENCE: 42

```
cagcaccatc agggctggca gcatagtaca tttcatctga c                          41
```

<210> SEQ ID NO 43
<211> LENGTH: 23
<212> TYPE: DNA
<213> ORGANISM: Artificial Sequence
<220> FEATURE:
<223> OTHER INFORMATION: Primer for PCR amplification

<400> SEQUENCE: 43

```
cgttgtggct gttgtagttg tac                                              23
```

<210> SEQ ID NO 44
<211> LENGTH: 22
<212> TYPE: DNA
<213> ORGANISM: Artificial Sequence
<220> FEATURE:
<223> OTHER INFORMATION: primer for PCR amplification

<400> SEQUENCE: 44

```
tgcggcggat ttatcttgca ag                                               22
```

<210> SEQ ID NO 45

```
<211> LENGTH: 40
<212> TYPE: DNA
<213> ORGANISM: Artificial Sequence
<220> FEATURE:
<223> OTHER INFORMATION: Primer for PCR amplification

<400> SEQUENCE: 45
cagccctgat ggtgctggac tatttaggac caccgtagag                    40

<210> SEQ ID NO 46
<211> LENGTH: 28
<212> TYPE: DNA
<213> ORGANISM: Artificial Sequence
<220> FEATURE:
<223> OTHER INFORMATION: primer for PCR amplifiction

<400> SEQUENCE: 46
atatatgcgt gccgcgtggc ggatcccc                                 28

<210> SEQ ID NO 47
<211> LENGTH: 29
<212> TYPE: DNA
<213> ORGANISM: Artificial Sequence
<220> FEATURE:
<223> OTHER INFORMATION: Primer for PCR amplification

<400> SEQUENCE: 47
atatatcatg gtggctcgag ggtggtgtt                                29

<210> SEQ ID NO 48
<211> LENGTH: 38
<212> TYPE: DNA
<213> ORGANISM: Artificial Sequence
<220> FEATURE:
<223> OTHER INFORMATION: Primer for PCR amplification

<400> SEQUENCE: 48
caccatcagg gactacagca tagtacattt catctgac                      38

<210> SEQ ID NO 49
<211> LENGTH: 37
<212> TYPE: DNA
<213> ORGANISM: Artificial Sequence
<220> FEATURE:
<223> OTHER INFORMATION: Primer for PCR amplification

<400> SEQUENCE: 49
tagtccctga tggtgactat ttaggaccac cgtagag                       37

<210> SEQ ID NO 50
<211> LENGTH: 24
<212> TYPE: RNA
<213> ORGANISM: Artificial Sequence
<220> FEATURE:
<223> OTHER INFORMATION: Modified bacteriophage R17 replicase initiator
      oligoribonucleotide

<400> SEQUENCE: 50
auaguccagc accaucaggg cugg                                     24

<210> SEQ ID NO 51
<211> LENGTH: 20
<212> TYPE: RNA
<213> ORGANISM: Artificial Sequence
<220> FEATURE:
<223> OTHER INFORMATION: Modified bacteriophage R17 replicase initiator
      oligoribonucleotide
```

```
<400> SEQUENCE: 51
auagucacca ucagggacua                                                         20
```